(12) United States Patent
Jozefiak et al.

(10) Patent No.: US 7,048,917 B1
(45) Date of Patent: May 23, 2006

(54) FAT-BINDING POLYMERS

(75) Inventors: Thomas Jozefiak, Watertown, MA (US); Stephen Randall Holmes-Farley, Arlington, MA (US); W. Harry Mandeville, III, Lynnfield, MA (US); Chad Cori Huval, Somerville, MA (US); Venkata R. Garigapati, Waltham, MA (US); Keith K. Shackett, Athol, MA (US); Danny Concagh, Watertown, MA (US)

(73) Assignee: Genzyme Corporation, Cambridge, MA (US)

( * ) Notice: Subject to any disclaimer, the term of this patent is extended or adjusted under 35 U.S.C. 154(b) by 719 days.

(21) Appl. No.: 09/721,291

(22) Filed: Nov. 22, 2000

Related U.S. Application Data

(60) Division of application No. 09/353,329, filed on Jul. 14, 1999, now Pat. No. 6,299,868, which is a continuation-in-part of application No. 09/166,453, filed on Oct. 5, 1998, now Pat. No. 6,264,937, which is a continuation-in-part of application No. 09/004,963, filed on Jan. 9, 1998, now abandoned.

(51) Int. Cl.
- A61K 31/795 (2006.01)
- A61K 31/785 (2006.01)
- A61K 31/74 (2006.01)

(52) U.S. Cl. ............... 424/78.35; 424/78.01; 424/78.36; 424/78.31; 514/449; 514/909

(58) Field of Classification Search ............ 424/78.01, 424/78.35, 78.31, 78.36; 514/909, 449; 525/295
See application file for complete search history.

(56) References Cited

U.S. PATENT DOCUMENTS

| | | | |
|---|---|---|---|
| 3,780,171 A | 12/1973 | Irmscher et al. | 424/79 |
| 3,923,972 A | 12/1975 | Fields et al. | 424/78 |
| 4,160,826 A | 7/1979 | Fischetti | 424/180 |
| 4,211,765 A | 7/1980 | Johnson et al. | 424/78 |
| 4,218,443 A | 8/1980 | Comai et al. | 424/181 |
| 4,265,879 A | 5/1981 | Fields et al. | 424/78 |
| 4,302,450 A | 11/1981 | Comai et al. | 424/181 |
| 4,432,968 A | 2/1984 | Page et al. | 424/78 |
| 4,598,089 A | 7/1986 | Hadvary et al. | 514/449 |
| 4,959,179 A | 9/1990 | Aronson et al. | 252/135 |
| 5,063,210 A | 11/1991 | Lange, III et al. | 514/54 |
| 5,089,163 A | 2/1992 | Aronson et al. | 252/135 |
| 5,137,716 A | 8/1992 | Weisenfeld | 424/78.01 |
| 5,200,183 A | 4/1993 | Tang et al. | 424/94.6 |
| 5,286,481 A | 2/1994 | Weisenfeld | 424/78.01 |
| 5,308,766 A | 5/1994 | Dennis et al. | 435/184 |
| 5,376,674 A | 12/1994 | Derungs et al. | 514/422 |
| 5,401,498 A | 3/1995 | Kesseler et al. | 424/78.11 |
| 5,427,919 A | 6/1995 | Dennis et al. | 435/18 |
| 5,453,282 A | 9/1995 | Kanauchi et al. | 424/464 |
| 5,453,429 A | 9/1995 | Bliem et al. | 514/288 |
| 5,474,993 A | 12/1995 | Rubin et al. | 514/192 |
| 5,484,777 A | 1/1996 | Lange, III et al. | 514/54 |
| 5,567,597 A | 10/1996 | Dennis et al. | 435/18 |
| 5,569,452 A | 10/1996 | Amidon et al. | 424/78.1 |
| 5,597,810 A | 1/1997 | Hoffman et al. | 514/54 |
| 5,607,669 A | 3/1997 | Mandeville, III et al. | 424/78.12 |
| 5,618,530 A | 4/1997 | Mandeville, III et al. | 424/78.12 |
| 5,624,963 A | 4/1997 | Mandeville, III et al. | 514/789 |
| 5,665,348 A | 9/1997 | Okayama et al. | 424/78.35 |
| 5,679,717 A | 10/1997 | Mandeville, III et al. | 514/742 |
| 5,693,675 A | 12/1997 | Mandeville, III et al. | 514/742 |
| 5,703,188 A | 12/1997 | Mandeville, III et al. | 526/290 |
| 5,750,524 A | 5/1998 | Mera et al. | 514/247 |
| 5,900,233 A | 5/1999 | Day | 424/78.01 |
| 5,900,475 A | 5/1999 | Mandeville, III et al. | 528/392 |
| 6,030,953 A | 2/2000 | Bailly et al. | 514/25 |
| 6,299,868 B1 | 10/2001 | Jozefiak et al. | 424/78.35 |
| 6,358,522 B1 | 3/2002 | Hug et al. | 424/441 |

FOREIGN PATENT DOCUMENTS

| | | |
|---|---|---|
| EP | 0 050 347 | 4/1982 |
| EP | 0 381 262 | 8/1990 |
| FR | 2 081 400 | 12/1971 |
| JP | 04333694 | * 11/1992 |
| JP | 06 321787 | 11/1994 |
| WO | WO 89/07455 | 8/1989 |

OTHER PUBLICATIONS

CAPLUS Abstract, AN 1993:256861, JP 04333694, 1992, Niike et al.*
CAS registry 147867-87-6.*
Gargouri, Y., et al., "Ajoene prevents fat digestion by human gastric lipase in vitro," *Biochimica et Biophysica Acta.* 1006:137-139 (1989).

(Continued)

*Primary Examiner*—Shengjun Wang
(74) *Attorney, Agent, or Firm*—Fish & Neave IP Group Ropes & Gray LLP

(57) ABSTRACT

The present invention relates to a method for treating obesity, a method for reducing the absorption of dietary fat, and a method for treating hypertriglyceridemia in a patient and to particular polymers for use in the methods or in a manufacture of a medicament. The methods comprise the step of orally administering to a mammal, such as a human, a therapeutically effective amount of one or more fat-binding polymers. The administration of the fat-binding polymer of the invention facilitates the removal of fat from the body prior to digestion, with minimal side effects and low toxicity. In a preferred embodiment, the one or more fat-binding polymers are administered in combination with one or more lipase inhibitors, for example, lipstatin and tetrahydrolipstatin.

13 Claims, No Drawings

OTHER PUBLICATIONS

Gargouri, Y., et al., "Covalent inhibition of digestive lipases: an in vitro study," *Biochimica et Biophysica Acta. 1344*:6-37 (1997).

Karamać, M. and Amarowicz, R., "Inhibition of Pancreatic Lipase by Phenolic Acids, Examination in vitro," *Verlag der Zeitschrift für Naturforschung*:903-905 (1996).

Marguet, F., et al., "Digestive lipases: inactivation by phosphonates," *Biochimica et Biophysica Acta. 1210*:157-166 (1994).

Mannesse, M.L.M., et al., "Phosphonate analogues of triacylglycerols are potent inhibitors of lipase," *Biochimica et Biophysica Acta. 1259*:56-64 (1995).

Martichonok, V. and Jones, J.B., "(Z)-Heptadec-8-enylboronic acid: a potential lipase inhibitor," *J. Chem. Soc. Perkin Trans. 1*:2927-2929 (1995).

Vainio, P., et al., "Inhibition of Lipoprotein Lipase by Benzene Boronic Acid Effect of Apolipoprotein C-II," *Biochimica et Biophysica Acta. 711*:386-390 (1982).

Bagree, A., et al., "Modification of ε-Amino Group of Lysine in Proteins by Acylation with Pyromellitic Dianhydride and o-Sulphobenzoic Anhydride," *FEBS Letters* 120 (2):275-277 (1980).

Stadler, P., et al., "Inhibition of microbial lipases with stereoisomeric triradylglycerol analog phosphonates," *Biochimica et Biophysica Acta. 1304*:229-244 (1996).

Kawaguchi, K., et al. Hesperidin as an Inhibitor of Lipases from Procine Pancreas and *Pseudomonas, Biosci. Biotech. Biochem. 61*(1):102-104 (1997).

Bochenek, W.J. and Rodgers, J.B., "Effect of Polyol Detergents on Cholesterol and Triglyceride Absorption," *Biochimica et Biophysica Acta 489*:503-506 (1977).

Comai, K. and Sullivan, A.C., "Antiobesity activity of pluronic L-101," *International Journal of Obesity 4*:33-42 (1980).

Han, L-K, et al., "Reduction in fat storage during chitin-chitosan treatment in mice fed a high-fat diet," *International Journal of Obesity 23*:174-179 (1999).

Atkinson, et al., "Combined drug treatment of obesity," *Obesity Research,* vol. 3, No. S4:497S-500S (1995).

Sjöström, et al., "Randomised placebo-controlled trial of orlistat for weight loss and prevention of weight regain in obese patients," *The Lancet,* 352:167-172 (1998).

* cited by examiner

FAT-BINDING POLYMERS

RELATED APPLICATIONS

This application is a Divisional of U.S. application Ser. No. 09/353,329, filed Jul. 14, 1999, now U.S. Pat. No. 6,299,868, which is a Continuation-in-part of U.S. application Ser. No. 09/166,453 filed on Oct. 5, 1998, now U.S. Pat. No. 6,624,937, which is a Continuation-in-Part of U.S. application Ser. No. 09/004,963 filed on Jan. 9, 1998 now abandoned, the entire contents of which are hereby incorporated by reference.

BACKGROUND OF THE INVENTION

Human obesity is a recognized health problem with approximately 97 million people considered clinically overweight in the United States. The accumulation or maintenance of body fat bears a direct relationship to caloric intake. Therefore, one of the most common methods for weight control to combat obesity is the use of relatively low-fat, low calorie diets, that is, diets containing less fat and calories than a "normal diet" or that amount generally consumed by the patient.

The presence of fats in a great many food sources greatly limits the food sources which can be used in a low-fat diet. Additionally, fats contribute to the flavor, appearance and physical characteristics of many foodstuffs. As such, the acceptability of low-fat diets and the maintenance of such diets are difficult.

Various chemical approaches have been proposed for controlling obesity. Anorectic agents, such as dextroamphetamine, the combination of the non-amphetamine drugs phentermine and fenfluramine ("Phen-Fen") and dexfenfluramine (Redux) alone, are associated with serious side effects. Indigestible materials such as OLESTRA™, mineral oil or neopentyl esters (see U.S. Pat. No. 2,962,419) have been proposed as substitutes for dietary fat. Garcinia acid and derivatives thereof have been described as treating obesity by interfering with fatty acid synthesis. Swellable crosslinked vinyl pyridine resins have been described as appetite suppressants via the mechanism of providing non-nutritive bulk, as in U.S. Pat. No. 2,923,662. Surgical techniques, such as temporary ileal bypass surgery, are employed in extreme cases.

However, methods for treating obesity, such as those described above, have serious shortcomings with controlled diet remaining the most prevalent technique for controlling obesity. As such, new methods for treating obesity are needed.

SUMMARY OF THE INVENTION

The present invention relates to a method for treating obesity, a method for reducing the absorption of dietary fat, and a method for treating hypertriglyceridemia in a patient and to particular polymers for use in the methods or in a manufacture of a medicament. The methods comprise the step of orally administering to a mammal, such as a human, a therapeutically effective amount of a fat-binding polymer. The administration of a fat-binding polymer of the invention facilitates the excretion of fat from the body without digestion, with minimal side effects and low toxicity. In a preferred embodiment, the fat-binding polymers are administered in combination with a therapeutically effective amount of a lipase inhibitor, such as the pancreatic lipase inhibitors described in U.S. Pat. No. 4,598,089 to Hadvary et al. The combination administration can reduce undesirable side effects often encountered when lipase inhibitors, in particular, the pancreatic lipase inhibitors lipstatin and tetrahydrolipstatin are administered alone. For example, a serious side effect resulting from the administration of a lipase inhibitor is steatorrhea, or fatty stools.

The fat-binding polymers of the invention comprise at least one fat-binding region. A fat-binding region can include a region having a positive charge, a region which is hydrophobic or a region having a positive charge and which is hydrophobic.

In one embodiment, the fat-binding polymer is an aliphatic polymer selected from the group consisting of polyalkylacrylates, polyacrylamides, polyalkylmethacrylates, polymethacrylamides, poly-N-alkylacrylamides, poly-N-alkylmethacrylamides, substituted derivatives thereof and copolymers thereof. For example, the substituted derivatives of the polymers can be characterized by one or more substituents, such as substituted or unsubstituted, saturated or unsaturated alkyl, and substituted or unsubstituted aryl groups. Suitable substituents to employ on the alkyl or aryl groups include, but are not limited to, cationic or neutral groups, such as alkoxy, aryl, aryloxy, aralkyl, halogen, amine, and ammonium groups. For example, the polymer can be poly(dimethylamino propylacrylamide), poly(trimethylammonium ethylacrylate), poly(trimethylammonium ethyl methacrylate), poly(trimethylammonium propyl acrylamide), poly(dodecyl acrylate), poly(octadecyl acrylate), poly(octadecyl methacrylate) and copolymers thereof.

In another embodiment, the fat binding polymer is a synthetic amine polymer and pharmaceutically acceptable salts thereof. Amine polymers (or salts thereof) suitable for use in the invention include, but are not limited to, substitued or unsubstituted polymers or copolymers of the following monomers: allylamine, diallyldimethyl ammonium, ethyleneimine, vinylamine, diallylamine, vinylimidazole and diallylmethylamine.

In another embodiment, the fat binding polymer is an amine derivative of an anhydride containing polymer.

In yet another embodiment, the fat-binding polymer is a hydroxyl-containing polymer, for example, poly(vinylalcohol).

In a specific embodiment, the fat-binding polymer is an amine-containing polymer wherein one or more hydrophobic regions are bound to a portion of the amine nitrogens of the amine polymer. In a particular embodiment, between about 1 and about 60 percent of the amine nitrogens are substituted, preferably between about 1 and about 30 percent.

In another embodiment, the hydrophobic region of the fat-binding polymer can include a hydrophobic moiety, for example, a substituted or unsubstituted, normal, branched or cyclic alkyl group having at least four carbons. In a particular embodiment, the hydrophobic moiety is an alkyl group of between about four and thirty carbons.

In another embodiment, the hydrophobic region is a quaternary amine-containing moiety having a terminal hydrophobic substituent. Suitable hydrophobic regions which can include a hydrophobic moiety and/or a quaternary amine-containing moiety are described herein and in U.S. Pat. Nos. 5,607,669, 5,679,717 and 5,618,530, the entire contents of which are incorporated herein by reference in their entirety.

The polymers of the present invention offer desirable pharmacological properties such as excellent fat binding properties and low toxicity. In addition, when the fat-binding polymers are administered in combination with lipase inhibitors, as described herein, undesirable side effects experienced, such as steatorrhea, when the lipase inhibitors are administered alone can be lessened.

DETAILED DESCRIPTION OF THE INVENTION

The features and other details of the invention will now be more particularly described and pointed out below as well as in the claims. It will be understood that the particular embodiments of the invention are shown by way of illustration and not as limitations of the invention. The principle features of this invention can be employed in various embodiments without departing from the scope of the invention.

In one aspect, the invention relates to a method for treating obesity comprising the step of orally administering to a mammal a therapeutically effective amount of one or more fat-binding polymers. In a preferred embodiment, the fat-binding polymer is administered in combination with a therapeutically effective amount of a lipase inhibitor.

In another aspect, the invention relates to a method for reducing the absorption of dietary fat comprising the step of orally administering to a mammal a therapeutically effective amount of one or more fat-binding polymers. In a preferred embodiment, the fat-binding polymer is administered in combination with a therapeutically effective amount of a lipase inhibitor.

In yet another aspect, the invention relates to a method for treating hypertriglyceridemia in a mammal comprising the step of orally administering to a mammal a therapeutically effective amount of one or more fat-binding polymers. In a preferred embodiment, the fat-binding polymer is administered in combination with a a therapeutically effective amount of a lipase inhibitor.

A particular aspect of the invention relates to a method for treating steatorrhea comprising the step of orally administering to a mammal a therapeutically effective amount of a fat-binding polymer. In a specific embodiment, the steatorrhea is a result of the administration of a lipase inhibitor.

The invention also relates to fat-binding polymers useful in the method of the invention.

"Lipases" as that term is used herein, are ubiquitous enzymes which hydrolyze ester bonds in neutral lipids. Examples of lipases include, but are not limited to, pancreatic and gastric lipases. The preferred substrates of lipases are insoluble in water. Lipases exhibit maximal activity in the presence of lipid/water interfaces. For example, pancreatic lipase, which is the key enzyme of dietary triglyceride absorption, exerts it activity at the water/lipid interface, in conjunction with bile salts and co-lipase.

"Lipase inhibitor" as that term is used herein refers to compounds which are capable of inhibiting the action of lipases, for example, gastric and pancreatic lipases. Lipstatin and its tetrahydro derivative, Tetrahydrolipstatin, as described in U.S. Pat. No. 4,598,089 to Hadvary et al., the entire content of which is hereby incorporated by reference, are potent inhibitors of both gastric and pancreatic lipases, as well as cholesterol ester hydrolase. Lipstatin is a natural product of microbial origin, and tetrahydrolipstatin is the result of catalytic hydrogenation of lipstatin. Other lipase inhibitors include a class of compound commonly referred to as Panclicins. Panclicins are analogues of Tetrahydrolipstatin (See e.g., Mutoh, M., et al., "Panclicins, Novel Pancreatic Lipase Inhibitors, II. Structural Elucidation," *The Journal of Antibiotics,* 47(12): 1376–1384 (1994), the entire content of which is hereby incorporated by reference.)

"Fat-binding polymers", as that term is used herein, are polymers which absorb, bind or otherwise associate with fat thereby inhibiting (partially or completely) fat digestion, hydrolysis, or absorption in the gastrointestinal tract and/or facilitate the removal of fat from the body prior to digestion. The fat-binding polymers comprise one or more fat-binding regions. "Fat-binding regions", as defined herein can include a positively charged region, a hydrophobic region, or a region which is both positively charged and hydrophobic.

"Fats", as that term is used herein, are solids or liquid oils generally consisting of glycerol esters of fatty acids. Sources of fats include both animal and vegetable fats, for example, triglyceride esters of saturated and/or unsaturated fatty acids, free fatty acids, diglycerides, monoglycerides, phospholipids and cholesterol esters are fats, as defined herein.

A variety of polymers can be employed in the invention described herein. The polymers are synthetic polymers which can be aliphatic, or aromatic. However, aliphatic and synthetic polymers are preferred. A "synthetic polymer", as that term is employed herein, is a polymer which is not obtainable from a natural source either directly or through a minor derivatization of the naturally occurring form. Further, the polymer can be hydrophobic, hydrophilic or copolymers of hydrophobic and/or hydrophilic monomers. Particularly preferred polymers comprise monomers having both cationic and hydroxy functional groups, and/or comprise a combination of separate monomers each having either a cationic or hydroxy functional group. Other preferred polymers comprise monomers having both cationic and hydrophobic groups, and/or comprise a combination of separate monomers each having either a cationic or a hydrophobic functional groups. As used herein the term "combination of monomers" or "combination of repeat units" means that at least one of each monomer or at least one of each repeat unit are present in the resulting polymerized polymer in any order. Many polymers can be conveniently manufactured from olefinic or ethylenic monomers (such as vinylalcohol, allylamine or acrylic acid) or condensation polymers. Examples of the preparation of preferred polymers of the invention are included in Examples 1–98.

For example, the polymers can include substituted or unsubstituted polyvinylalcohol, polyvinylamine, poly-N-alkylvinylamine, polyallylamine, poly-N-alkylallylamine, polydiallylamine, poly-N-alkyldiallylamine, polyalkylenimine, other polyamines, polyethers, polyamides, polyacrylic acids, polyalkylacrylates, polyacrylamides, polymethacrylic acids, polyalkylmethacrylates, polymethacrylamides, poly-N-alkylacrylamides, poly-N-alkylmethacrylamides, polystyrene, polyvinylnaphthalene, polyethylvinylbenzene, polyaminostyrene, polyvinylbiphenyl, polyvinylanisole, polyvinylimidazolyl, polyvinylpyridinyl, polydimethylaminomethylstyrene, polydiallylmethylammonium chloride, polytrimethylammonium ethyl methacrylate, polytrimethylammonium ethyl acrylate, and copolymers thereof. In addition, the polymers can be further characterized by one or more substituents such as substituted and unsubstituted, saturated or unsaturated alkyl, and substituted or unsubstituted aryl groups. Suitable groups to employ include cationic or neutral groups, such as alkoxy, aryl, aryloxy, aralkyl, halogen, amine, ammonium groups, substituted or unsubstituted oxypolyethylene oxide, and mono, di or higher hydroxyalkyl groups.

Particularly preferred polymers (or salts thereof) include substituted or unsubstituted polydiethylammonium chloride, polyvinylimidazole, polyalkylacrylates, polyacrylamides, polyalkylmethacrylates, polymethacrylamides, poly-N-alkylacrylamides, poly-N-alkylmethacrylamides and copolymers thereof. These polymers can be further characterized by one or more substituents such as those discussed above.

Other particularly preferred polymers include aliphatic amine polymers, such as polyallylamine, polydiallylamine, polydiallylmethylamine, polyvinylamine, polyethylenimine. In a specific embodiment, the amine polymer comprises one or more hydrophobic regions which are bound to a portion of the amine nitrogens of the amine polymer. In a particular embodiment, between about 1 and about 60 percent of the amine nitrogens are substituted, preferably between about 1 and about 30 percent.

Additional particularly preferred polymers include maleic anhydride and maleic anhydride olefinic copolymers, itaconic anhydride, and amine derivatives thereof. The amine derivatives may preferably contain dimethyl amino groups.

In one embodiment, the hydrophobic region of the fat-binding polymer can include a hydrophobic moiety, for example, a substituted or unsubstituted, normal, branched or cyclic alkyl group having at least four carbons. In a specific embodiment, the hydrophobic moiety is an alkyl group of between about four and thirty carbons.

In another embodiment, the hydrophobic region is a quaternary amine-containing moiety having a terminal hydrophobic substituent.

In yet another embodiment, the fat-binding region comprises a nitrogen, for example, the nitrogen of an amine, capable of possessing a positive charge under conditions present in the gastro-intestinal tract. For example, a quaternary amine-containing moiety, or the nitrogen of a polyamine.

In yet another embodiment, the fat-binding polymer is a hydroxyl-containing polymer, for example, poly(vinylalcohol) which can comprise further fat-binding regions. For example, the polymer comprises a repeat unit having the formula

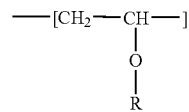

wherein R is a hydrophobic region.

Preferred polymers are copolymers that comprise both cationic monomers such as those containing nitrogen, and monomers with hydroxy groups.

Other polymers and methods of preparation, which can be used in the claimed invention have been reported in the patent literature in, for example, U.S. Pat. Nos. 5,487,888, 5,496,545, 5,607,669, 5,618,530, 5,624,963, 5,667,775, and 5,679,717 and co-pending U.S. applications having Ser. Nos. 08/471,747, 08/482,969, 08/567,933, 08/659,264, 08/823,699, 08/835,857, 08/470,940, 08/461,298, 08/826,197, 08/777,408, 08/927,247, 08/964,956, 08/964,498, and 08/964,536, the entire contents of all of which are incorporated herein by reference.

The polymer can be linear or crosslinked. Crosslinking can be performed by reacting the copolymer with one or more crosslinking agents having two or more functional groups, such as electrophilic groups, which react with, for example, amine groups to form a covalent bond. Crosslinking in this case can occur, for example, via nucleophilic attack of the polymer amino groups on the electrophilic groups. This results in the formation of a bridging unit which links two or more amino nitrogen atoms from different polymer strands. Suitable crosslinking agents of this type include compounds having two or more groups selected from among acyl chloride, epoxide, and alkyl-X, wherein X is a suitable leaving group, such as a halo, tosyl or mesyl group. Examples of such compounds include, but are not limited to, epichlorohydrin, succinyl dichloride, acryloyl chloride, butanedioldiglycidyl ether, ethanedioldiglycidyl ether, pyromellitic dianhydride, and dihaloalkanes. These crosslinking agents are referred to herein as multifunctional crosslinking agents.

The polymer composition can also be crosslinked by including a multifunctional co-monomer as the crosslinking agent in the polymerization reaction mixture. A multifunctional co-monomer can be incorporated into two or more growing polymer chains, thereby crosslinking the chains. Suitable multifunctional co-monomers include, but are not limited to, diacrylates, triacrylates, and tetraacrylates, dimethacrylates, diacrylamides, and dimethacrylamides. Specific examples include ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), pentaerythritol tetraacrylate, trimethylolpropane triacrylate, bisphenol A dimethacrylate, and bisphenol A diacrylate. Other suitable multifunctional monomers include polyvinylarenes, such as divinylbenzene.

The amount of cross-linking agent is typically between about 0.01 and about 10 weight % based on the combined weight of crosslinking agent and monomers, with 0.1–3% being preferred. Typically, the amount of cross-linking agent that is reacted with the polymer, when the crosslinking agent is a multifunctional agent, is sufficient to cause between about 0.1 and 6 percent of the nucleophiles present on the monomer, for example, an amine to react with the crosslinking agent.

The hydrophobic region or regions of the fat-binding polymers include but are not limited to, for example, a hydrophobic moiety such as a substituted or unsubstituted, normal, branched or cyclic alkyl group having at least about four carbons and preferably at least 6 carbons. For example, a hydrophobic moiety such as an alkyl group of at least four carbons and preferably at least 6 carbons can be bound to the fatbinding polymer, for example, through an amine of the fat-binding polymer.

A "hydrophobic moiety (group)", as the term is used herein, is a moiety which, as a separate entity, is more soluble in octanol than water. For example, the octyl group ($C_8H_{17}$) is hydrophobic because its parent alkane, octane, has greater solubility in octanol than in water. The hydrophobic moieties can be a saturated or unsaturated, substituted or unsubstituted hydrocarbon group. Such groups include substituted and unsubstituted, normal, branched or cyclic alkyl groups having at least four carbon atoms, substituted or unsubstituted arylalkyl or heteroarylalkyl groups and substituted or unsubstituted aryl or heteroaryl groups. Preferably, the hydrophobic moiety includes an alkyl group of between about four and thirty carbons. Specific examples of suitable hydrophobic moieties include the following alkyl groups n-hexyl, n-heptyl, n-octyl, n-nonyl, n-decyl, n-undecyl, n-dodecyl, n-tetradecyl, n-octadecyl, 2-ethylhexyl, 3-propyl-6-methyl decyl, phenyl and combinations thereof. Other examples of suitable hydrophobic moieties include haloalkyl groups of at least six carbons (e.g., 10-halodecyl), hydroxyalkyl groups of at least six carbons (e.g., 11-hydroxyundecyl), and aralkyl groups (e.g., benzyl).

The positiviely charged region or regions of the fat binding polymers may include primary, secondary, tertiary or quaternary amines. Optionally, the positively charged region or regions of the fat-binding polymers may include an amine nitrogen capable of possessing a positive charge under conditions present in the gastro-intestinal tract and a quaternary amine-containing moiety. Suitable quaternary amine-containing moieties used in conjunction with acrylate or acrylamide polymers, for example, include alkyl trialkylammonium groups also referred to as ammonioalkyl groups. The term, "ammonioalkyl", as used herein, refers to an alkyl group which is substituted by a nitrogen bearing three additional substituents. Thus, the nitrogen atom is an ammonium nitrogen atom which bears an alkylene substituent, which links the ammonium nitrogen atom to the polymer, and three additional terminal alkyl substituents having from about one to about twenty-four carbons. A "terminal substituent" of the quaternary amine-containing moiety, as the term is employed herein, is any one of the three substituents on the quaternary amine nitrogen. In a specific embodiment, the polymer is an amine polymer and the alkylene group links the ammonium nitrogen atom to the nitrogen atom of the polymer. It is to be understood that multiple moieties can be bound to the same amine and/or different amines of the polymer composition.

In another embodiment, the quaternary amine-containing moiety can bear at least one terminal hydrophobic alkyl substituent, such as an alkyl group having between about four and twenty-four carbons, thereby providing both a hydrophobic region and a positively charged region in combination.

An ammonioalkyl group will further include a negatively charged counterion, such as a conjugate base of a pharmaceutically acceptable acid. Examples of suitable counterions include $Cl^-$, $PO_4^-$, $Br^-$, $CH_3SO_3^-$, $HSO_4^-$, $SO_4^{2-}$, $HCO_3^-$, $CO_3^{2-}$, acetate, lactate, succinate, propionate, butyrate, ascorbate, citrate, maleate, folate, tartrate, polyacrylate, an amino acid derivative, and a nucleotide.

Suitable ammonioalkyl groups are of the general formula:

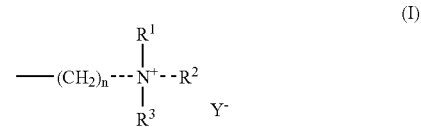

(I)

wherein, $R^1$, $R^2$ and $R^3$ represent an alkyl group, wherein each $R^1$–$R^3$, independently, is a normal or branched, substituted or unsubstituted alkyl group having a carbon atom chain length of between about one to about twenty-four carbon atoms, n is an integer having a value of two or more and Y is a negatively charged counterion. In a particular embodiment, $R^1$, $R^2$ and $R^3$ are all methyl groups and n is an integer between about 2 and about 12. Examples of preferred alkylene linking groups are ethyl, propyl, butyl, pentyl, hexyl, octyl, and decyl groups. Example of suitable quaternary amine-containing moieties include, but are not limited to:

3-(trimethylammonio)propyl;
4-(trimethylammonio)butyl;
6-(trimethylammonio)hexyl;
8-(trimethylammonio)octyl;
10-(trimethylammonio)decyl;
12-(trimethylammonio)dodecyl and combinations thereof. A particularly preferred amine-containing moiety is a 6-(trimethylammonio)hexyl group.

Alternatively, a quaternary amine-containing moiety and a hydrophobic moiety are present in the same substituent, thereby providing both a positively charged and hydrophobic region in combination. For example, the quaternary amine nitrogen or ammonium nitrogen of the quaternary amine-containing moiety is bound to the polymer backbone by an alkylene having two or more carbons. However, at least one of the three terminal substituents ($R^1$, $R^2$ and $R^3$) of the ammonium nitrogen is a hydrophobic alkyl group having from four to about twenty-four carbons. The remaining terminal substituents are each independently a normal or branched, substituted or unsubstituted alkyl group having from one to about twenty-four carbons or a hydrogen atom. In another embodiment, at least two of the three terminal substituents can be hydrophobic alkyl groups having from four to about twenty-four carbons, the remainder having from one to about twenty-four carbons or a hydrogen atom.

In a further embodiment, all three of the terminal substituents can be hydrophobic alkyl groups having from six to about twenty-four carbons.

A "hydrophobic alkyl group", as that term is employed herein, includes a substituted or unsubstituted alkyl group having from four to about twenty-four carbons and which is hydrophobic, as earlier defined. The hydrophobic alkyl group can be, for example, a normal or branched, substituted or unsubstituted alkyl group having from six to about twenty-four carbons.

Particular examples of quaternary amine-containing moieties, which provide both a hydrophobic and quaternary amine-containing substituent, include, but are not limited to:
4-(dioctylmethylammonio)butyl;
3-(dodecyldimethylammonio)propyl;
3-(octyldimethylammonio)propyl;
3-(decyldimethylammonio)propyl;
5-(dodecyldimethylammonio)pentyl;
6-(dimethyldecylammonio)hexyl;
6-(decyldimethylammonio)hexyl;
3-(tridecylammonio)propyl;
3-(docosyldimethylammonio)propyl;
6-(docosyldimethylammonio)hexyl;
4-(dodecyldimethylammonio)butyl;
3-(octadecyldimethylammonio)propyl;
3-(hexyldimethylammonio)propyl;
3-(methyldioctylammonio)propyl;
3-(didecylmethylammonio)propyl;
3-(heptyldimethylammonio)propyl;
3-(dimethylnonylammonio)propyl;
6-(dimethylundecylammonio)hexyl;
4-(heptyldimethylammonio)butyl;
4-(dioctylmethylammonio)butyl;
6-(octyldimethylammonio)hexyl;
12-(decyldimethylammonio)dodecyl;
3-(dimethylundecylammnio)propyl; and
3-(tetradecyldimethylammonio)propyl.

Other suitable quaternary amine-containing moieties include secondary and tertiary analogs, such as 4-(dioctylmethylammonio)4-methylbutyl and 4(dioctylmethylammonio)-4,4-dimethylbutyl.

The fat-binding polymers of the invention can be formed, for example, by reacting a polymer, which can be linear or crosslinked, with a suitable alkylating agent or by polymerizing an alkylated monomer.

An "alkylating agent", as that term is employed herein, means a reactant that, when reacted with a monomer or a copolymer characterized by a repeat unit of the invention and having a nucleophilic site capable of reaction with the alkylating agent, causes a hydrophobic substituent, as described herein, to be covalently bound to one or more of sites on the fat-binding polymer, for example, the amine nitrogen atoms or hydroxyl oxygens of an amine-containing or hydroxyl-containing monomer or polymer, respectively. Further, when multiple substituents are employed, they can be bound to the same and/or different nucleophilic sites of the fat-binding polymer, for example, the same and/or different amine nitrogens of an amine-containing fat-binding polymer or hydroxyloxygen of a hydroxyl-containing polymer.

Suitable alkylating agents are compounds comprising an alkyl group or alkyl derivative, having at least four carbon atoms, which is bonded to a leaving group such as a halo (e.g., chloro, bromo or iodo), tosylate, mesylate or epoxy group).

Examples of suitable alkylating agents which provide a hydrophobic moiety include alkyl halides having at least four carbon atoms, such as n-hexyl halide, n-heptyl halide, n-octyl halide, n-nonyl halide, n-decyl halide, n-undecyl halide, n-dodecyl halide, n-tetradecyl halide, n-octadecyl halide, and combinations thereof. Other examples include: a dihaloalkane that includes an alkyl group of at least four carbons (e.g., a 1,10-dihalodecane); a hydroxyalkyl halide having at least four carbon atoms (e.g., an 11-halo-1-undecanol); an aralkyl halide (e.g., a benzyl halide); an alkyl epoxy ammonium salt having at least six carbons (e.g., glycidylpropyl-trimethylammonium salts) and epoxyalkylamides having at least six carbons (e.g., N-(2,3-epoxypropyl) butyramide or N-(2,3-epoxypropyl) hexanamide). Preferred halogen components of the alkyl halides are bromine and chlorine. Particularly preferred alkylating agents which, when reacted with the polymer composition, will cause formation of an amine polymer reaction product that includes a first substituent, are 1-bromodecane and 1 chlorooctane.

Examples of suitable alkylating agents which can provide a quaternary amine-containing moiety have the general formula:

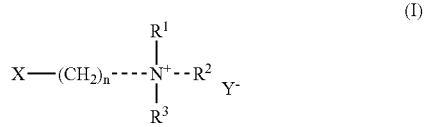

(I)

wherein,
$R^1$, $R^2$, and $R^3$ represent an alkyl group, wherein each R independently is a normal or branched, substituted or unsubstituted alkyl group having a carbon atom chain length of between about one to about twenty four carbon atoms,
n is an integer having a value of two or more,
X is a leaving group as earlier described, and
Y is a negatively charged counterion.

When at least one of the three terminal substituents of the quaternary amine alkylating agent is a hydrophobic alkyl group having from four to about twenty-four carbons, the alkylating agent therefore provides both a hydrophobic moiety and a quaternary amine-containing moiety. The alkylene group in this instance is three or more carbon atoms in length.

Particular examples of quaternary ammonium compounds suitable as alkylating agents include the following:
(4-bromobutyl)dioctylmethylammonium bromide;
(3-bromopropyl)dodecyldimethylammonium bromide;
(3-chloropropyl)dodecyldimethylammonium bromide;
(3-chloropropyl)decyldimethylammonium bromide;
(5-tosylpentyl)dodecyldimethylammonium bromide;
(6-bromohexyl)dimethyldecylammonium bromide;
(12-bromododecyl)decyldimethylammonium bromide;
(3-bromopropyl)tridecylammonium bromide;
(3-bromopropyl)docosyldimethylammonium bromide;
(6-bromohexyl)docosyldimethylammonium bromide;

(4-chlorobutyl)dodecyldimethylammonium bromide;
(3-chloropropyl)octadecyldimethylammonium bromide;
(3-bromopropyl)octyldimethylammonium bromide;
(4-iodobutyl)dioctylmethylammonium bromide;
(2,3-epoxy propyl)decyldimethylammonium bromide; and
(6-bromohexyl)docosyldimethyammonium bromide.

Other suitable alkylating agents include secondary and tertiary analogs, such as (3-bromobutyl)dioctylmethylammonium bromide and (3-chloro-3,3-dimethyl propyl)dioctylmethylammonium bromide.

Examples of suitable alkyl trimethylammonium alkylating agents include alkyl halide trimethylammonium salts, such as:
(4-halobutyl)trimethylammonium salt;
(5-halopentyl)trimethylammonium salt;
(6-halohexyl)trimethylammonium salt;
(7-haloheptyl)trimethylammonium salt;
(8-halooctyl)trimethylammonium salt;
(9-halononyl)trimethylammonium salt;
(10-halodecyl) trimethylammonium salt;
(11-haloundecyl)trimethylammonium salt;
(12-halododecyl)trimethylammonium salt; and combinations thereof. A particularly preferred quaternary amine-containing alkylating agent is (6-bromohexyl)-trimethylammonium bromide.

The fat-binding polymers of the invention can be formed, for example, by reacting a polymer, which can be linear or crosslinked, with a suitable modifying agent. A "modifying agent", as that term is employed herein, means a reactant that, when reacted with a monomer or a copolymer characterized by a repeat unit of the invention and having a nucleophilic site capable of reaction with the modifying agent, causes a hydrophobic substituent, as described herein, to be covalently bound to one or more of sites on the fat-binding polymer, for example, the amine nitrogen atoms of an amine-containing polymer. Further, when multiple substituents are employed, they can be bound to the same and/or different nucleophilic sites of the fat-binding polymer, for example, the same and/or different amine nitrogens of an amine-containing fat-binding polymer.

Suitable modifying agents are compounds comprising substituted alkyl group or alkyl aromatic groups which is bonded to a leaving group such as a halo (e.g., chloro, bromo or iodo), tosylate, mesylate or epoxy group). Examples of suitable modifying agents which provide a hydrophilic moiety include haloalkanols, (for example, 2-bromoethanol, 3-bromopropanol, 4-bromobutanol, 4-chlorobutanol and 3-bromo-2-hydroxy propanol), haloalkanoic acids (for example chloracetic acid, bromoacetic acid, 3-bromo propionic acid and 4-bromobutyric acid, glycidol, glycidyl trimethylammonium chloride, and ethylene oxide. Particularly preferred modifying agents which include glycidol, and 2-bromoethanol.

Preferred fat binding polymers, copolymers or salts thereof in accordance with the invention are described in Examples 1–98.

Even more preferred fat binding polymers, copolymers (and/or salts thereof) of the invention comprises at least one repeat unit or a combination of repeat units selected from the following group of repeat unit formulas, or combinations of repeat unit formulas.

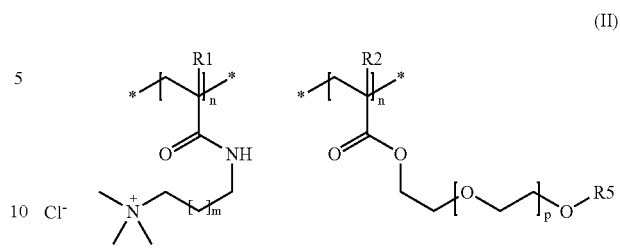

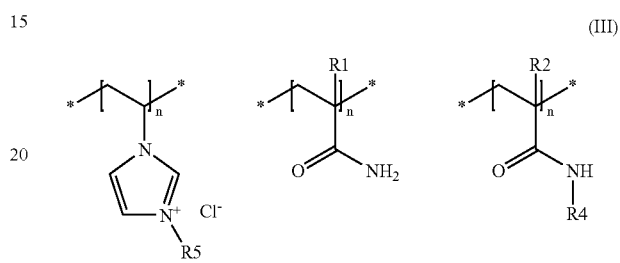

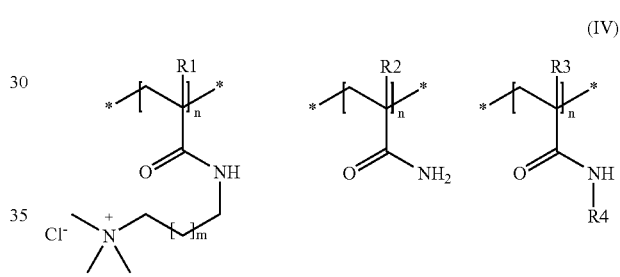

wherein

R1=H, or $CH_3$,

R2=H, or $CH_3$,

R3=H, or $CH_3$,

R4=a hydrophobic group, and m=0–4

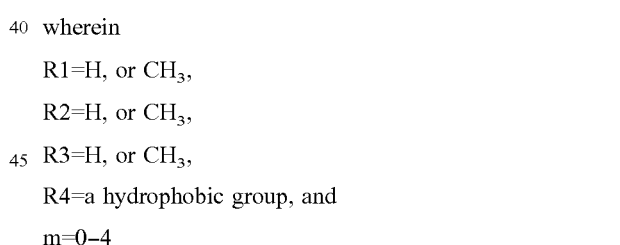

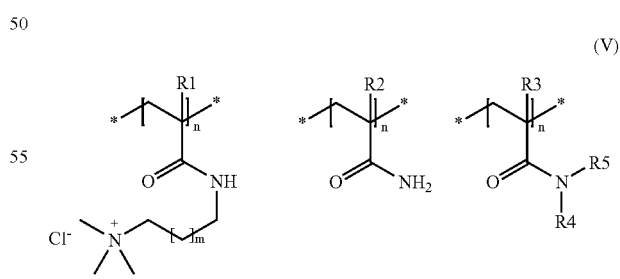

wherein

R1=H, or $CH_3$,

R2=H, or $CH_3$,

R3=a hydrophobic group,

R4=a hydrophobic group,
R5=an alkyl chain from $C_1$ to $C_{22}$ and
m=0–4

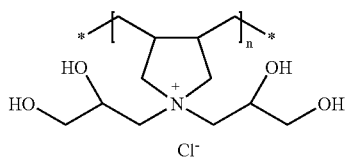
(VI)

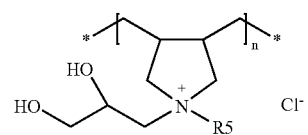
(VII)

Wherein R5=H, or an alkyl chain from $C_1$ to $C_{22}$

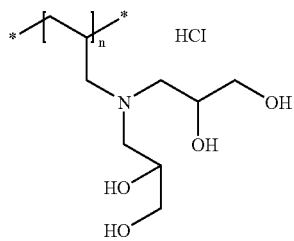
(VIII)

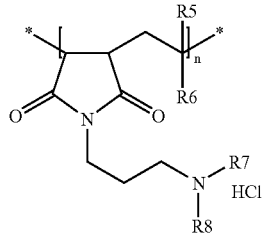
(IX)

wherein
R5=H, or an alkyl chain from $C_1$ to $C_{22}$,
R6=H, or an alkyl chain from $C_1$ to $C_{22}$
R7=H, or an alkyl chain from $C_1$ to $C_{22}$
R8=H, or an alkyl chain from $C_1$ to $C_{22}$

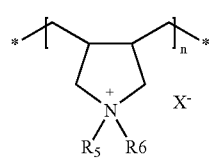
(X)

wherein
R5=H, or an alkyl chain from $C_1$ to $C_{22}$,
R6=H, or an alkyl chain from $C_1$ to $C_{22}$, and wherein
X=a pharamaceutically acceptable anion Particularly preferred fat binding polymers, copolymers (and/or salts thereof) of the invention comprise the following:

A polymer of Formula II wherein: R1=H, R2=H, R5=CH$_3$, m=1, p=about 114 and wherein the resulting polymer may be expressed as Poly((3-acrylamidopropyl)trimethylammonium chloride-co-O-acryloyl-O'-methylpolyethyleneglycol 5000). Preferably, such polymer contains 11 wt % of the PEG-containing monomer;

A polymer of Formula III wherein R1=H, R2=H, R4=$C_{12}H_{25}$, R5=CH$_3$ and wherein the resulting polymer may be expressed as Poly(3-methyl-1-vinylimidazolium chloride-co-acrylamide-co-dodecyl acrylamide). Even more preferably, such polymer has a monomer mole ratio of 35/70/5;

A polymer of Formula IV wherein R1=H, R2=H, R3=H, R4=$C_6H_5$ (phenyl), m=1 and wherein the resulting polymer may be expressed as Poly((3-acrylamidopropyl)trimethylammonium chloride-co-acrylamide-co-N-phenylacrylamide). Even more preferably, such polymer has a Mol % monomer composition of 25/70/5;

A polymer of Formula V wherein R1=H, R2=H, R3=H, R4=$C_{18}H_{37}$, R5=CH$_3$, m=1 and wherein the resulting polymer may be expressed as Poly((3-acrylamidopropyl)trimethylammonium chloride-co-acrylamide-co-N-methyl-N-octadecylacrylamide). Even more preferably such polymer has a Mol % monomer composition of 25/70/5;

The polymer of Formula VI which may be expressed as Poly(N,N-diallyl-N,N-di(2,3-dihydroxypropyl)ammonium chloride);

The polymer of Formula VII wherein R5=methyl and wherein such polymer may be expressed as Poly(N,N-diallyl-N-methyl-N-(2,3-dihydroxypropyl) ammonium chloride);

The polymer of Formula VII which may be expressed as Poly(N,N-di(2,3-dihydroxypropyl)allylamine) hydrochloride;

A polymer of Formula IX wherein, R5=H, R6=H, R7=CH$_3$, R8=CH$_3$ and wherein such polymer may be expressed as Poly(N-(3-dimethylaminopropyl)maleimide-co-ethylene) hydrochloride;

A Polymer of Formula X wherein R5=H, R6=CH$_3$, X=tartrate, and wherein such polymer may be expressed as Poly(N-methyl-N,N-diallylammonium) tartrate.

In addition, another particularly preferred polymer of the invention may be expressed as Polyethyleneimine 80% ethoxylated, the structure of which is understood in the art.

Exemplative synthetic schemes for each of the preferred and particularly preferred polymers of the invention may be found in the Examples and particularly in Examples.

In another embodiment, the fat-binding polymer can have a lipase inhibitor covalently bound to the polymer as described in PCT/US99/00195. In a further embodiment, the fat-binding polymer can be administered in combination with a lipase inhibitor which is covalently bound to a polymer as described in PCT/US99/00195, the entire content of which is incorporated herein by reference.

As used herein, the terms "therapeutically effective amount" and "therapeutic amount" are synonymous. The terms refer to an amount which is sufficient to treat obesity, reduce the absorption of fat or treat hypertriglyceridemia. The dosage of fat-binding polymer administered to the patient will vary depending among other things on the weight of the patient and the general health of the patient. The dosage can be determined with regard to established medical practice. The amount of fat-binding polymer administered can be in the range of from about 0.01 mg/kg of body weight/day to about 1 g/kg of body weight/day. The amount of lipase inhibitor which can be administered in combination with the fat-binding polymers of the invention can be determined with regard to accepted medical practice (e.g. the Physicians Desk Reference).

As disclosed above, in a preferred embodiment, the preferred and particularly preferred fat-binding polymers in accordance with the invention are administered in combination with a lipase inhibitor, as described herein. The term "in combination" in this context includes both simultaneous or sequential administration (either type of compound first) of the fat-binding polymer and lipase inhibitor. The fat-binding polymer and lipase inhibitor, when used in combination, can be employed together in the same dosage form or in separate dosage forms taken at the same time or within a time period, wherein both the fat-binding polymer and lipase inhibitor are present in a therapeutically effective amount.

The fat-binding polymers of the invention can be formulated using conventional inert pharmaceutical adjuvant materials into dosage forms which are suitable for oral administration. The oral dosage forms include tablets, capsules, suspension, solutions, and the like. The identity of the inert adjuvant materials which are used in formulating the fat-binding polymers of the invention will be immediately apparent to persons skilled in the art. These adjuvant materials, either inorganic or organic in nature, include, for example, gelatin, albumin, lactose, starch, magnesium stearate, preservatives (stabilizers), melting agents, emulsifying agents, salts, and buffers.

In patients with hypertriglyceridemia it is to be understood that the patient does not necessarily suffer from hypercholesterolemia.

EXAMPLES

Example 1

Poly((3-acrylamidopropyl)trimethylammonium chloride-co-acrylamide-co-N-decylacrylamide) Mol % monomer composition: 25/70/5

A 250-mL round-bottomed flask was fitted with an overhead stirrer, a reflux condenser, and a thermocouple probe. The following materials were placed into the flask in the order specified: a solution of decylacrylamide (2.83 g, 0.0134 mole) in tert-butanol (45 mL), 3-acrylamidopropyltrimethylammonium chloride (18.45 g of a 75 percent solution in water, 0.067 mole), deionized water (40 mL), and acrylamide (13.33 g, 0.1875 mole). The resulting mixture was stirred and heated to 50° C. A clear, slightly yellow solution resulted. The solution was sparged for at least 30 minutes with a vigorous nitrogen flow from an 18-gauge syringe needle whose tip was placed below the surface of the stirring solution. The radical initiator 2,2'azobis(2-amidinopropane) dihydrochloride (0.363 g, 0.00134 mole) was then added to the solution and the temperature was increased to 60° C. The solution was stirred at 60° C. for 14–16 hours. The solution was then cooled to room temperature and poured into 3 L of isopropanol, resulting in precipitation of the polymeric product as a colorless solid. This mixture was stirred for 1–3 hours, and the isopropanol was decanted away from the polymer product. A fresh 3-L portion of isopropanol was then added, and the mixture was stirred for 3–6 hours. Again, the isopropanol was decanted away, and another 3-L portion of fresh isopropanol was added to the polymer. The mixture was stirred for 6–14 hours and the isopropanol was decanted away from the polymer product. The polymer was placed on a glass tray, and dried in a forced-air oven at 70° C. for 24–48 hours. The dried solid was then ground to a fine powder using a commercial coffee grinder. The fine powder was placed into a glass tray in a forced air oven at 70° C. for at least 24 hours. A colorless solid (30.04 g) was obtained.

Example 2

Poly((3-acrylamidopropyl)trimethylammonium chloride-co-acrylamide-co-N-decylacrylamide) Mol % monomer composition: 25/65/10

The procedure of example 1 was followed substituting the following materials and amounts: decylacrylamide (5.33 g, 0.0252 mole), 3-acrylamidopropyltrimethylammonium chloride (17.37 g of a 75 percent solution in water, 0.063 mole), deionized water (40.5 mL), acrylamide (11.65 g, 0.1638 mole), 2,2'azobis(2-amidinopropane) dihydrochloride (0.342 g, 0.00126 mole). The amount of polymer obtained was 30.7 g.

Example 3

Poly((3-acrylamidopropyl)trimethylammonium chloride-co-acrylamide-co-N-decylacrylamide) Mol % monomer composition: 25/60/15

The procedure of example 1 was followed substituting the following materials and amounts: decylacrylamide (7.55 g, 0.0357 mole), 3-acrylamidopropyltrimethylammonium chloride (16.4 g of a 75 percent solution in water, 0.060 mole), deionized water (41 mL), acrylamide (10.15 g, 0.1428 mole), 2,2'azobis(2-amidinopropane) dihydrochloride (0.332 g, 0.00119 mole). The amount of polymer obtained was 25.6 g.

Example 4

Poly((3-acrylamidopropyl)trimethylammonium chloride-co-acrylamide-co-N,N-didecylacrylamide) Mol % monomer composition: 25/70/5

The procedure of example 1 was followed substituting the following materials and amounts: didecylacrylamide (3.69 g, 0.0105 mole) in tert-butanol (37 mL), 3-acrylamidopropyltrimethylammonium chloride (14.48 g of a 75 percent solution in water, 0.053 mole), deionized water (34.4 mL), acrylamide (10.15 g, 0.147 mole), 2,2'azobis(2-amidinopropane) dihydrochloride (0.285 g, 0.00105 mole). The amount of polymer obtained was 23.62 g.

Example 5

Poly((3-acrylamidopropyl)trimethylammonium Chloride-co-acrylamide-co-N-phenylacrylamide) Mol % monomer composition: 75/20/5

The procedure of example 1 was followed substituting the following materials and amounts: phenylacrylamide (1.04 g, 0.0071 mole) in tert-butanol (37.5 mL), 3-acrylamidopropyltrimethylammonium chloride (29.27 g of a 75 percent solution in water, 0.106 mole), deionized water (30 mL), acrylamide (2.01 g, 0.028 mole), 2,2'azobis(2-amidinopropane) dihydrochloride (0.192 g, 0.00071 mole). The amount of polymer obtained was 26.1 g.

Example 6

Poly((3-acrylamidopropyl)trimethylammonium chloride-co-acrylamide-co-N-benzylacrylamide) Mol % monomer composition: 75/20/5

The procedure of example 1 was followed substituting the following materials and amounts: benzylacrylamide (0.91 g, 0.0056 mole) in tert-butanol (51 mL), 3-acrylamidopropyltrimethylammonium chloride (23.32 g of a 75 percent solution in water, 0.085 mole), deionized water (40 mL), acrylamide (1.60 g, 0.023 mole), 2,2'azobis(2-amidinopropane) dihydrochloride (0.192 g, 0.00056 mole). The amount of polymer obtained was 17.8 g.

Example 7

Poly((3-acrylamidopropyl)trimethylammonium chloride-co-N-tert-octylacrylamide) Mol % monomer composition: 90/10

The procedure of example 1 was followed using the following reagents: N-tert-octylacrylamide (2.24 g, 0.0122 mole) in tert-butanol (50 g), 3-acrylamidopropyltrimethylammonium chloride (30.25 g of a 75 percent solution in water, 0.110 mole), deionized water (50 mL), 2,2'azobis(2-amidinopropane) dihydrochloride (0.166 g, 0.00061 mole). The amount of polymer obtained was 21.2 g.

Example 8

Poly((3-acrylamidopropyl)trimethylammonium Chloride-co-N-butylacrylamide) Mol % monomer composition: 25/75

The procedure of example 1 was followed using the following reagents: N-butylacrylamide (5.06 g, 0.04 mole) in tert-butanol (13.38 g), 3-acrylamidopropyltrimethylammonium chloride (3.65 g of a 75 percent solution in water, 0.013 mole), deionized water (8.9 mL), 2,2'azobis(2-amidinopropane) dihydrochloride (0.072 g, 0.00027 mole). The amount of polymer obtained was 4.00 g.

Example 9

Poly(2-(Methacryloyloxy)ethyl-tert-butylamine hydrochloride)

The procedure of example 1 was followed using the following reagents: 2(Methacryloxy)ethyl-tert-butylamine (30 g, 0.162 mole) in tert-butanol (68 mL), deionized water (22 mL), 2,2'azobis(2-amidinopropane) dihydrochloride (0.220 g, 0.00081 mole). The solvent used for precipitation and washing of the polymer was hexane. The amount of polymer obtained was 21.9 g.

Example 10

Poly((3-acrylamidopropyl)trimethylammonium chloride-co-styrene) Mol % monomer composition: 60/40

The procedure of example 1 was followed using the following reagents: styrene (5.03 g, 0.048 mole) in ethanol (80 mL), 3-acrylamidopropyltrimethylammonium chloride (19.96 g of a 75 percent solution in water, 0.072 mole), 2,2'-azobisisobutyronitrile (0.198 g, 0.0012 mole). The solvent used for precipitation and washing of the polymer was acetone. The amount of polymer obtained was 14.5 g.

Example 11

Poly((3-methacrylamidopropyl)trimethylammonium chloride-co-poly(dimethylsiloxane)monomethacrylate) Wt % monomer composition: 90/10

The procedure of example 1 was followed using the following reagents: poly(dimethylsiloxane)monomethacrylate (Mn=9,000–12,000) (0.60 g) in isopropanol (18.6 mL), 3-methacrylamidopropyltrimethylammonium chloride (10.8 g of a 50 percent solution in water, 0.072 mole), 2,2'-azobisisobutyronitrile (0.030 g, 0.00018 mole). The solvent used for precipitation and washing of the polymer was isopropanol. The amount of polymer obtained was 4.13 g.

Example 12

Poly((3-acrylamidopropyl)trimethylammonium chloride-co-acrylamide-co-N-octadecylacrylamide) Mol % monomer composition: 60/35/5

The procedure of example 1 was followed substituting the following materials and amounts: octadecylacrylamide (79.38 g, 0.2453 mole) in isopropanol (3081.2 g), 3-acrylamidopropyltrimethylammonium chloride (811.41 g of a 75 percent solution in water, 2.944 mole), deionized water (406 mL), and acrylamide (122.06 g, 1.717 mole), 2,2'-azobisisobutyronitrile (4.029 g, 0.0245 mole) in tetrahydrofuran (46 g). The amount of polymer obtained was 815 g.

Example 13

Poly((3-acrylamidopropyl)trimethylammonium chloride-coacrylamide-co-N-phenylacrylamide) Mol % monomer composition: 25/70/5

The procedure of example 1 was followed substituting the following materials and amounts: phenylacrylamide (33.82 g, 0.230 mole) in tert-butanol (1000 g), 3-acrylamidopropyltrimethylammonium chloride (316.7 g of a 75 percent solution in water, 1.149 mole), deionized water (921 mL), acrylamide (228.67 g, 3.217 mole), 2,2'azobis(2-amidinopropane) dihydrochloride (3.323 g, 0.0230 mole) in deionized water (24 g). The amount of polymer obtained was 532 g.

Example 14

Poly((3-acrylamidopropyl)trimethylammonium chloride-coacrylamide-co-N-methyl-N-octadecylacrylamide) Mol % Monomer Composition: 25/70/5

The procedure of example 1 was followed using the following reagents: N-methyl-N-octadecylacrylamide (134.96 g, 0.400 mole) in tert-butanol (1892 g), 3-acrylamidopropyltrimethylammonium chloride (550.9 g of a 75 percent solution in water, 2.00 mole), deionized water (1754 mL), and acrylamide (397.83 g, 5.597 mole), 2,2'azobis(2-amidinopropane) dihydrochloride (6.163 g, 0.040 mole) in deionized water (32 g). The amount of polymer obtained was 1046 g.

Example 15

Poly(3-methyl-1-vinylimidazolium chloride-co-acrylamide-co-dodecylacrylamide) monomer mole ratio: 35/70/5

In a 500-mL flask equipped with an overhead mechanical stirrer and a thermocouple probe, 1-vinylimidazole (270 g, 2.869 mole) was dissolved in 2.7 L of anhydrous ethyl acetate. The solution was cooled to −10° C., and methyl iodide was added (1425 g, 10.04 mole). Throughout the reaction the temperature was maintained at −10° C. using an ice salt bath. After the addition was complete, the reaction mixture was stirred for 1 hour at −10° C., then brought to room temperature and allowed to stir for 16 hours. During this time off-white crystals formed in the solution. The mixture was filtered and the crystalline solid was washed with 10 L of anhydrous diethyl ether. This off-white solid was then recrystallized from n-propanol (melting point 68° C.). The crystalline solid was then dissolved in 2.4 L of methanol to which was added 3.7 kg of Amberlite IRA-400 chloride ion exchange resin. The slurry was stirred for 4 hours and then filtered. The filtrate was then concentrated under vacuum and then placed on a high vacuum pump to remove any remaining solvent. The amount of 3-methyl-1-vinylimidazole chloride obtained was 347.76 g. The procedure of example 1 was followed using the following reagents: dodecylacrylamide (104.1 g, 0.435 mole) in tert-butanol (856 g), 3-methyl-1-vinylimidazolium chloride (619 g of a 71.1 percent solution in water, 3.0434 mole), deionized water (888.1 mL), acrylamide (370.9 g, 5.217 mole), 2,2'azobis(2-amidinopropane) dihydrochloride (11.8 g, 0.04348 mole). The amount of polymer obtained was 813 g.

Example 16

Poly((3-acrylamidopropyl)trimethylammonium chloride-coacrylamide) Mol % monomer composition: 50/50

A 5000-mL round-bottomed flask was fitted with an overhead stirrer, a reflux condenser, and a thermocouple probe. The following materials were placed into the flask in the order specified: 3-acrylamidopropyltrimethylammonium chloride (396.86 g of a 75 percent solution in water, 1.44 mole), deionized water (1500 mL), and acrylamide (102.35 g, 1.44 mole). The resulting mixture was stirred at approximately 23° C. A clear, slightly yellow solution resulted. The solution was sparged for at least 60 minutes with a vigorous nitrogen flow from an 18-gauge syringe needle whose tip was placed below the surface of the stirring solution. Potassium metabisulfite (0.213 g, 0.00096 mole) and potassium persulfate (0.259, 0.00096 mole) were then each separately dissolved in a small amount of water and added individually to the solution. After 2–10 minutes, the temperature was increased to 60° C. The solution was stirred at 60° C. for 5–6 hours. The flask was then fitted with a distillation head and the solution was heated to 95° C. The vigorous nitrogen flow was resumed and 500 mL of water was distilled out of the flask in order to facilitate the work-up procedure. The polymer solution was cooled and poured into 22 L of isopropanol, resulting in precipitation of the polymeric product as a colorless solid. This mixture was stirred overnight, and the isopropanol was decanted away from the polymer product. A fresh portion of isopropanol was then added, and the mixture was stirred for 48 hours and the isopropanol was decanted away from the polymer product. The polymer was placed on a glass tray, and dried in a forced-air oven at 70° C. for 24–48 hours. The dried solid was then ground to a fine powder using a commercial coffee grinder. The fine powder was placed into a glass tray in a forced air oven at 70° C. for 24–48 hours. A colorless solid (390.5 g) was obtained.

Example 17

Poly((3-acrylamidopropyl)trimethylammonium chloride)

The procedure of example 16 was followed using the following reagents: 3-acrylamidopropyltrimethylammonium chloride (533.3 g of a 75 percent solution in water, 1.94 mole), deionized water (1467 mL), potassium metabisulfite (0.143 g, 0.00065 mole) and potassium persulfate (0.174, 0.00065 mole). The amount of polymer obtained was 372 g.

Example 18

Poly((3-acrylamidopropyl)trimethylammonium chloride-co-N-vinyl-2-pyrrolidinone) Mol % monomer composition: 80/20

A 1000-mL round-bottomed flask was fitted with an overhead stirrer, a reflux condenser, and a thermocouple probe. The following materials were placed into the flask in the order specified: 3-acrylamidopropyltrimethylammonium chloride (141.04 g of a 75 percent solution in water, 0.512 mole), deionized water (511 mL), and N-vinyl-2-pyrrolidinone (14.22 g, 0.128 mole). The resulting mixture was stirred at approximately 23° C. A clear, slightly yellow solution resulted. The solution was sparged for at least 60 minutes with a vigorous nitrogen flow from an 18-gauge syringe needle whose tip was placed below the surface of the stirring solution. The radical initiator 2,2'azobis(2-amidinopropane) dihydrochloride (1.20 g, 0.0044 mole) was then added to the solution and the temperature was increased to 60° C. The solution was stirred at 60° C. overnight. The solution was cooled to room temperature and diluted with 600 mL of deionized water. The solution was then poured into a series of cellulose dialysis bags (Spectra/Por, molecular weight cutoff=6000–8000), and exhaustively dialysed against deionized water. The polymer solution was removed from the dialysis bags, placed in a glass tray, and dried in a forced-air oven at 70° C. for 24–48 hours. The dried solid was then ground to a fine powder using a commercial coffee grinder. The fine powder was placed into a glass tray in a forced air oven at 70° C. for 24–48 hours. A colorless solid (78 g) was obtained.

Example 19

Poly((3-acrylamidopropyl)trimethylammonium chloride-co-N-ethylacrylamide) Mol % monomer composition: 50/50

A 250-mL round-bottomed flask was fitted with an overhead stirrer, a reflux condenser, and a thermocouple probe. The following materials were placed into the flask in the order specified: 3-acrylamidopropyltrimethylammonium chloride (19.36 g of a 75 percent solution in water, 0.065 mole), deionized water (80 mL), and N-ethylacrylamide (6.48 g, 0.0654 mole). The resulting mixture was stirred at approximately 23° C. A clear, slightly yellow solution resulted. The solution was sparged for at least 30 minutes with a vigorous nitrogen flow from an 18-gauge syringe needle whose tip was placed below the surface of the stirring solution. The radical initiator 2,2'azobis(2-amidinopropane) dihydrochloride (0.177 g, 0.00065 mole) was then added to the solution and the temperature was increased to 60° C. The solution was stirred at 60° C. until it became a thick gel. The solution was then cooled to room temperature and poured into 3 L of isopropanol, resulting in precipitation of the polymeric product as a colorless solid. This mixture was stirred overnight, and the isopropanol was decanted away from the polymer product. A fresh 3-L portion of isopropanol was then added, and the mixture was stirred for 6–8 hours. Again, the isopropanol was decanted away. The polymer was placed on a glass tray, and dried in a forced-air oven at 70° C. for 24–48 hours. The dried solid was then ground to a fine powder using a commercial coffee grinder. The fine powder was placed into a glass tray in a forced air oven at 70° C. for at least 24 hours. A colorless solid (15.5 g) was obtained.

Example 20

Poly(diallyldimethylammonium chloride-co-acrylic acid) monomer mole ratio: 90/10

The procedure of example 19 was followed using the following reagents: diallyldimethylammonium chloride (1465.9 g of a 65 percent solution in water, 5.89 mole), deionized water (3486.9 mL), acrylic acid (47.19 g, 0.655 mole), 2,2'azobis(2-amidinopropane) dihydrochloride (8.88 g, 0.0327 mole). The amount of polymer obtained was 632 g.

Example 21

Poly((3-acrylamidopropyl)trimethylammonium chloride-co-O-acryloyl-O'-methylpolyethylene glycol 5,000) Wt % monomer composition: 89/11

A procedure similar to example 19 was followed using the following reagents: 3-acrylamidopropyltrimethylammonium chloride (1187 g of a 75 percent solution in water, 4.31 mole), deionized water (3703 mL), and O-acryloyl-O'-methylpolyethylene glycol 5,000 (109.7 g, 0.022 mole), 2,2'azobis(2-amidinopropane) dihydrochloride (5.869 g, 0.0216 mole) in deionized water (30 g). The amount of polymer obtained was 928 g.

Example 22

Poly(3-methyl-1-vinylimidazolium chloride-co-acrylamide) monomer mole matio: 50/50

The procedure of example 19 was followed using the following reagents: 3-methyl-1-vinylimidazolium chloride (268.18 g, 1.855 mole), deionized water (933 mL), acrylamide (131.8 g, 1.855 mole), 2,2'azobis(2-amidinopropane) dihydrochloride (5.030 g, 0.0186 mole). The amount of polymer obtained was 382 g.

Example 23

Poly(N,N-diallyl-2-hydroxyethylamine)

A 50-mL round-bottomed flask was fitted with a magnetic stirrer, a reflux condenser, and a thermocouple probe. The following materials were placed into the flask in the order specified: N,N-diallyl-2-hydroxyethylamine (10 g), concentrated HCl (7 g), deionized water (3 mL). The solution was degassed for 30 minutes by bubbling with nitrogen from an 18-gauge needle. 2,2'Azobis(2-amidinopropane) dihydrochloride (0.095 g, 0.00035 mole) was then added and the solution was heated to 60° C. The solution was stirred at 60° C. overnight. The solution was then cooled to room temperature and poured into 1 L of isopropanol, resulting in precipitation of the polymeric product as a colorless solid.

This mixture was stirred for 1–3 hours, and the isopropanol was decanted away from the polymer product. A fresh 1-L portion of isopropanol was then added, and the mixture was stirred for 3–6 hours. Again, the isopropanol was decanted away, and another 1-L portion of fresh isopropanol was added to the polymer. The mixture was stirred overnight and the isopropanol was decanted away from the polymer product. The polymer was placed on a glass tray, and dried in a forced-air oven at 70° C. for 24–48 hours. The dried solid was then ground to a fine powder using a commercial coffee grinder. The fine powder was placed into a glass tray in a forced air oven at 70° C. for at least 24 hours. A colorless solid (8 g) was obtained.

No Examples 24 and 25

Example 26

Modification of poly(2-ethyl-2-oxazoline) by partial hydrolysis

A 250-mL flask was equipped with an overhead mechanical stirrer, condenser and a thermocouple probe. The following materials were placed into the flask in the order specified: poly(2-ethyl-2-oxazoline) (25 g), deionized water (95 mL), concentrated HCl (9.8 g). The solution was heated to reflux with stirring for 8 hours. The solution was then poured into 1.5 L of acetone resulting in the precipitation of the polymeric product. The mixture was stirred for 1 hour. The acetone was then decanted away and a fresh 1.5-L portion of acetone was added. After 2 hours of stirring, the acetone was decanted away, and the solid was blended in a commercial blender containing fresh acetone. The solid was collected by filtration and suspended in fresh acetone overnight. The solid was then collected and placed on a glass tray, and dried in a forced-air oven at 70° C. for 24–48 hours. The dried solid was then ground to a fine powder using a commercial coffee grinder. The fine powder was placed into a glass tray in a forced air oven at 70° C. for at least 24 hours. A colorless solid (30.04 g) was obtained.

Example 27

Modification of poly(allylamine) HCl with 100 mol % glycidol

Poly(allylamine) HCl (60 g of 50 percent aqueous solution, 0.321 mole monomer equivalents) was dissolved in 80 mL of water and was then heated to 50° C. in a 500-mL flask equipped with an overhead mechanical stirrer, condenser and a thermocouple probe. The pH of the solution was adjusted to 10 by the addition of NaOH (50 percent solution). Glycidol (23.77 g 0.321 mol) was added slowly to the stirred solution. A large exotherm was observed during the addition of the glycidol. This mixture was then heated at 50° C. for 3 hours giving a very viscous solution. The reaction mixture was cooled and then poured into a dialysis bag (Spectra/Por; molecular weight cut off 6000–8000) and dialyzed against 19 liters of deionized water. The dialysis solution was changed until a conductivity of <1 mS/cm was recorded. The contents of the dialysis bag were then placed in a beaker and the pH of the solution adjusted to a value <2 with concentrated HCl. This solution was then transferred to drying trays and placed in a convection oven at 70° C. for 24 hours. The dried solid was ground to a fine powder using a lab mill and then passed through a sieve (80 mesh). The product was then replaced in a convection oven at 70° C. for 48 hours to remove any residual solvent. Yield=47.2 g.

Example 28

Modification of poly(allylamine) HCl with 200 mol % glycidol

The procedure of example 27 was followed using the following materials: Poly(allylamine) HCl (60 g of 50 percent aqueous solution, 0.321 mole monomer equivalents), deionized water (80 mL), glycidol (47.54 g, 0.642 mole). The amount of polymer obtained was 66.8 g.

Example 29

Modification of poly(allylamine) HCl with 300 mol % glycidol

The procedure of example 27 was followed using the following materials: Poly(allylamine) HCl (40 g of 50 percent aqueous solution, 0.214 mole monomer equivalents), deionized water (80 mL), glycidol (47.54 g, 0.642 mole). The amount of polymer obtained was 48.9 g.

Example 30

Modification of poly(diallylamine) HCl with glycidol

The procedure of example 27 was followed using the following materials: Poly(diallylamine) HCl (106.8 g of 28.1 percent aqueous solution, 0.225 mole monomer equivalents), deionized water (43.2 mL), glycidol (41.57 g, 0.561 mole). The amount of polymer obtained was 56.3 g.

Example 31

40 Mol % modification of poly(diallylmethylamine) HCl with 2-chloroaceticic acid In a 500-mL flask equipped with an overhead mechanical stirrer, condenser and a thermocouple probe, poly(diallylmethylamine), (120 g of a 44.22 percent aqueous solution 0.359 mole monomer equivalents) was dissolved in 60 mL of deionized water and 225 mL ethanol. The solution was heated to 70° C. The pH of the solution was adjusted to 10 by the addition of NaOH (50 percent solution). 2-Chloroacetic acid (13.58 g, 0.144 mole) was then added in one portion. The reaction mixture was stirred at 70° C. for 16–18 hours. The pH of the solution was checked periodically during this time and was maintained at 10 by the addition of 50 percent NaOH. The solution was then cooled to room temperature, transferred to a dialysis bag (Spectra/Por molecular weight cut off 6000–8000) and dialyzed against 19 liters of deionized water. The dialysis solution was changed until a conductivity of <1 mS/cm was recorded. The contents of the dialysis bag was then placed in a beaker and the pH of the solution adjusted to a value <2 with concentrated HCl. This solution was then transferred to drying trays and placed in a convection oven at 70° C. for 24 hours. The dried solid was ground to a fine powder using a lab mill and then passed through a sieve (80 mesh). The product was then replaced in a convection oven at 70° C. for 48 hours to remove any residual solvent. The amount of polymer obtained was 55.5 g.

Example 32

30 Mol % Modification of poly(diallylmethylamine) HCl with 2-chloroaceticic acid The procedure of example 31 was followed using the following materials:
poly(diallylmethylamine) HCl (120 g of 44.22 percent aqueous solution, 0.359 mole monomer equivalents), deionized water (60 mL), ethanol (225 mL), 2-chloroacetic acid (10.19 g, 0.108 mole). The amount of polymer obtained was 53.8 g.

Example 33

20 Mol % Modification of poly(diallylmethylamine) HCl with 2-chloroaceticic acid The procedure of example 31 was followed using the following materials: poly(diallylmethylamine) HCl (62.9 g of 44.22 percent aqueous solution, 0.188 mole monomer equivalents), deionized water (30 mL), ethanol (110 mL), 2-chloroacetic acid (3.56 g, 0.038 mole). The amount of polymer obtained was 13.53 g.

Example 34

Modification of poly(diallylmethylamine) HCl with 3-bromopropionic acid

In a 500-mL flask equipped with an overhead mechanical stirrer, condenser and a thermocouple probe, poly(diallylmethylamine), (67.84 g of a 44.22 percent aqueous solution 0.203 mole monomer equivalents) was dissolved in 60 mL of deionized water and 120 mL ethanol. The solution was heated to 70° C. The pH of the solution was adjusted to 10 by the addition of NaOH (50 percent solution). 3-Bromopropionic acid (32.63 g, 0.213 mole) was then added in one portion. The reaction mixture was stirred at 70° C. for 16–18 hours. The pH of the solution was checked periodically during this time and was maintained at 10 by the addition of 50 percent NaOH. The solution was then cooled to room temperature, transferred to a dialysis bag (Spectra/Por molecular weight cut off 6000–8000) and dialyzed against 19 liters of deionized water. The dialysis solution was changed until a conductivity of <1 mS/cm was recorded. The contents of the dialysis bag was then placed in a beaker and the pH of the solution adjusted to a value <2 with concentrated HCl. This solution was then transferred to drying trays and placed in a convection oven at 70° C. for 24 hours. The dried solid was ground to a fine powder using a lab mill and then passed through a sieve (80 mesh). The product was then replaced in a convection oven at 70° C. for 48 hours to remove any residual solvent. The amount of polymer obtained was 35 g.

Example 35

Modification of poly(diallylmethylamine) HCl with 4-bromobutyric acid

The procedure of example 34 was followed using the following materials: poly(diallylmethylamine) HCl (67.84 g of 44.22 percent aqueous solution, 0.203 mole monomer equivalents), deionized water (60 mL), ethanol (130 mL), 4-bromobutyric acid (35.63 g, 0.213 mole). The amount of polymer obtained was 73 g.

Example 36

Modification of poly(allylamine) HCl with 3-bromopropionic acid

The procedure of example 34 was followed using the following materials: poly(allylamine) HCl (40 g of a 50 percent aqueous solution, 0.214 mole monomer equivalents), deionized water (50 mL), 3-bromopropionic acid (34.36 g, 0.225 mole). The amount of polymer obtained was 28.5 g.

Example 37

Modification of poly(allylamine) HCl with 4-bromobutyric acid

The procedure of example 34 was followed using the following materials: poly(allylamine) HCl (40 g of a 50 percent aqueous solution, 0.214 mole monomer equivalents), deionized water (50 mL), 4-bromobutyric acid (39.4 g, 0.236 mole). The amount of polymer obtained was 20.6 g.

Example 38

Modification of polyethylenimine with 3-bromopropionic acid

The procedure of example 34 was followed using the following materials: polyethylenimine (30 g of a 50 percent aqueous solution, 0.348 mole monomer equivalents), deionized water (45 mL), 3-bromopropionic acid (55.9 g, 0.365 mole). The amount of polymer obtained was 37.3 g.

Example 39

Polydiallylamine Hydrochloride

Diallylamine (2000.3 g) was added slowly over a period of 2 days to concentrated HCl (2035.6 g). The temperature of the reaction was maintained below 10° C. by cooling the flask in an ice-salt-water bath, and by adjusting the addition rate. The room temperature pH of the resulting diallylamine hydrochloride solution (68.16 percent diallylamine hydrochloride) was 0.005.

To a 12-L 4-necked round-bottomed flask equipped with an overhead stirrer and an air condenser, was added diallylamine hydrochloride (3667.8 g of a 68.16 percent solution), and deionized water (4665.5 g). The resulting solution had pH 0.74. To the flask was added NaOH (66.8 g of a 50 percent aqueous solution). The resulting solution had pH 2.55. Nitrogen gas was bubbled through the solution, via a stainless steel needle, with stirring, and venting on top of the air condenser for 2 hours. The nitrogen line was put on top of the air condenser with positive pressure from a mineral oil bubbler. To the flask was added 125.0 g of freshly made 20 percent 2,2'-azobis(2-amidinopropane) dihydrochloride in deionized water. This was added via syringe through a septum. The 2,2'-azobis(2-amidinopropane) dihydrochloride solution was not degassed with nitrogen. The solution was heated to 60° C. over a period of 1 hour 8 minutes., with a heating mantle connected to a J-Kem temperature controller. The solution was heated at 60° C. for 18 hours. The reaction temperature rose to 64° C., and slowly cooled back down to 60° C. over a 3 hours period. After the first 18-hour heating period, the reaction solution was allowed to cool down slowly to 49° C., and to the flask was added 125.0 g of freshly made 20 percent 2,2'-azobis(2-amidinopropane) dihydrochloride in deionized water. The solution was heated to 60° C. over a period of about 15 minutes, with a heating mantle connected to a J-Kem temperature controller. The solution was heated at 60° C. for 18 hours. The reaction temperature rose to 62° C., and slowly cooled back down to 60° C. over a 1 hour period. After the second 18 hours heating period, the reaction solution was allowed to cool down slowly to 40° C., and to the flask was added 125.0 g of freshly made 20 percent 2,2'-azobis(2-amidinopropane) dihydrochloride in deionized water. The solution was heated to 60° C. over a period of about 15 minutes, with a heating mantle connected to a J-Kem temperature controller. The solution was heated at 60° C. for 18 hours. The reaction temperature rose to 63° C., and slowly cooled back down to 60° C. over a 1 hour period. After cooling to room temperature, the solution was a dark orange viscous, flowable, clear solution. The flask contents were combined with deionized water (4166.7 g). The resulting solution had pH 4.41. SEC analysis: Mw 61,500 Daltons; polydispersity 2.43.

Example 40

Polydiallylmethylamine

Diallylmethylamine (361.0 g) was added slowly over a period of 2 hours, 10 minutes to concentrated HCl (320.3 g). The temperature of the reaction was maintained below 10° C. by cooling the flask in an ice-salt-water bath, and by adjusting the addition rate. The room temperature pH of the resulting diallylmethylamine hydrochloride solution was 6.492, and the solution had two phases, a small oil phase (top) with a large aqueous phase (bottom). To 660.5 g of this mixture was added concentrated HCl (22.6 g), and the pH of the final solution was 0.349. The final solution was a single phase, and contains 68.04 percent diallylmethylamine hydrochloride by weight.

To a 500-mL three-necked round-bottomed flask equipped with an overhead stirrer and a vigreux column, was added diallylmethylamine hydrochloride (73.5 g of a 68.04 percent solution), and deionized water (26.5 g). The resulting solution had pH 0.871. To the flask was added 50 percent aqueous NaOH until the resulting solution had pH 2.53. Nitrogen gas was bubbled through the solution, via a stainless steel needle, with stirring, and venting on top of the vigreux column for 30 minutes The nitrogen line was put on top of the vigreux column with positive pressure from a mineral oil bubbler. To the flask was added 2.5 g of freshly made 20 percent 2,2'-azobis(2-amidinopropane) dihydrochloride in deionized water. This was added via a transfer pipette, through one of the flask necks with a strong nitrogen flow. The 2,2'-azobis(2-amidinopropane) dihydrochloride solution was not degassed with nitrogen. The reaction solution was heated to 60° C. over a period of 30 minutes, with a heating mantle connected to a J-Kem temperature controller. The reaction solution was heated at 60° C. for 18 hours. After the first 18-hour heating period, the reaction solution was allowed to cool down slowly to room temperature, and to the flask was added 2.5 g of freshly made 20 percent 2,2'-azobis(2-amidinopropane) dihydrochloride in deionized water. The reaction solution was heated to 60° C. over a period of about 30 minutes. The reaction solution was heated at 60° C. for another 18 hours. After the second 18 hour heating period, the reaction solution was allowed to cool down slowly to room temperature, and to the flask was added 2.5 g of freshly made 20 percent 2,2'-azobis(2-amidinopropane) dihydrochloride in deionized water. The reaction solution was heated to 60° C. over a period of about 30 minutes. The reaction solution was heated at 60° C. for another 18 hours. After cooling to room temperature, the reaction solution was a clear dark orange, viscous and flowable solution. The flask contents were combined with deionized water (150.0 g). The resulting solution had pH 4.36. SEC analysis: Mw 54,100 Daltons; polydispersity 2.13.

Example 41

Functionalization of poly(ethylene-alt-maleic anhydride) with 3-(dimethylamino)propylamine To a solution of poly(ethylene-alt-maleic anhydride) (20.0 g) in N,N-dimethylformamide (180 mL) under a nitrogen atmosphere was added 3-(dimethylamino)propylamine (40 mL). The mixture was heated at 60° C. overnight and allowed to cool to room temperature. Concentrated HCl (47 g) was added and the mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. for 48 hours to afford 37.8 g.

No Example 42

Example 43

Functionalization of poly(diallylmethylamine) with polyoxyethylene(40) nonylphenyl glycidyl ether Polyoxyethylene(40) nonylphenyl glycidyl ether was synthesized by reacting polyoxyethylene(40) nonylphenyl ether (100.0 g) with epichlorohydrin (60 mL) in the presence of deionized water (0.750 g), NaOH (6 g), and 3,5-di-tert-butyl-4-hydroxyanisole (0.23 g) at 60° C. for 10 hours. After cooling to room temperature, methylene chloride (200 mL) was added, and this solution was extracted with a solution of deionized water (200 mL) and potassium dihydrogen phosphate (10 g). The organic layer was washed four times with deionized water (100 mL per wash) and concentrated on a rotary evaporator (60° C. bath temperature). The residue was triturated with diethyl ether (1 L) and dried under vacuum at 50° C. to afford 83.0 g.

A basic solution of polydiallylmethylamine was prepared by mixing polydiallylmethylamine hydrochloride (677 g of a 44.22 percent aqueous solution), deionized water (823 g) and NaOH (87 g of a 50 percent aqueous solution) overnight.

To a portion of the polydiallylmethylamine basic solution (158.9.0 g) was added polyoxyethylene(40) nonylphenyl glycidyl ether (3.0 g). After stirring overnight, concentrated HCl (25.0 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. for 48 hours to afford 31.5 g.

Example 44

Functionalization of poly(diallylmethylamine) with polyoxyethylene(40) nonylphenyl glycidyl ether To a portion of the polydiallylmethylamine basic solution (158.7 g; Example 43) was added polyoxyethylene(40) nonylphenyl glycidyl ether (6.0 g; Example 43). After stirring overnight, concentrated HCl (18.0 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 33.4 g.

Example 45

Functionalization of poly(diallylmethylamine) with polyoxyethylene(40) nonylphenyl gGlycidyl ether To a portion of the polydiallylmethylamine basic solution (158.7 g; Example 43) was added polyoxyethylene(40) nonylphenyl glycidyl ether (9.0 g; Example 43). After stirring overnight, concentrated HCl (32.6 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 37.3 g.

Example 46

Functionalization of poly(diallylmethylamine) with polyoxyethylene(40) nonylphenyl glycidyl ether To a portion of the polydiallylmethylamine basic solution (158.7 g; Example 43) was added polyoxyethylene(40) nonylphenyl glycidyl ether (12.0 g; Example 43). After stirring overnight, concentrated HCl (24.2 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 40.6 g.

Example 47

Functionalization of poly(diallylmethylamine) with polyoxyethylene(40) nonylphenyl glycidyl ether To a portion of the polydiallylmethylamine basic solution (158.7 g; Example 43) was added polyoxyethylene(40) nonylphenyl glycidyl ether (30 g; Example 43). After stirring overnight, concentrated HCl was added until the pH of the resulting solution was less than 1.0. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 60.0 g.

No Example 48

Example 49

Functionalization of poly(diallylmethylamine) with polyoxyethylene(23) lauryl glycidyl ether Polyoxyethylene (23) lauryl glycidyl ether was synthesized by reacting polyoxyethylene (23) lauryl ether (50.0 g) with epichlorohydrin (50 mL) in the presence of deionized water (0.625 g), NaOH (5 g), and 3,5-di-tert-butyl-4-hydroxyanisole (0.28 g) at 60° C. for 10 hours. After cooling to room temperature, methylene chloride (100 mL) was added, and this solution was extracted with a solution of deionized water (100 mL) and potassium dihydrogen phosphate (5 g). The organic layer was washed four times with deionized water (100 mL per wash) and concentrated on a rotary evaporator (60° C. bath temperature). The residue was triturated with diethyl ether (1 L) and dried under vacuum to afford 34.55 g.

A basic solution of polydiallylmethylamine was prepared by mixing polydiallylmethylamine hydrochloride (677 g of a 44.22 percent aqueous solution), deionized water (823 g) and NaOH (87 g of a 50 percent aqueous solution) overnight.

To a portion of the polydiallylmethylamine basic solution (158.7 g) was added polyoxyethylene(23) lauryl glycidyl ether (3.0 g). After stirring overnight, concentrated HCl (40.3 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 31 g.

Example 50

Functionalization of poly(diallylmethylamine) with polyoxyethylene(23) lauryl glycidyl ether To a portion of the basic solution of polydiallylmethylamine (158.7 g; Example 49) was added polyoxyethylene (23) lauryl glycidyl ether (6.0 g; Example 49). After stirring for 24 hours at room temperature, concentrated HCl (21.6 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 30.0 g.

Example 51

Functionalization of poly(diallylmethylamine) with glycidol

A basic solution of polydiallylmethylamine was prepared by mixing polydiallylmethylamine hydrochloride (615.4 g of a 44.22 percent aqueous solution), deionized water (745.2 g) and NaOH (78.0 g of a 50 percent aqueous solution) overnight.

To a portion of the basic solution of polydiallylmethylamine (158.7 g) was added glycidol (26.9 mL). After stirring for 24 hours at room temperature, concentrated HCl (14.2 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 40.0 g.

Example 52

Functionalization of poly(diallylmethylamine) with glycidol

To a portion of the basic solution of polydiallylmethylamine (158.7 g; Example 51) was added glycidol (13.5 mL). After stirring for 24 hours at room temperature, concentrated HCl (13.5 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 40.0 g.

Example 53

Functionalization of poly(diallylmethylamine)

To a portion of the basic solution of polydiallylmethylamine (158.7 g; Example 51) was added bromoethane (30.30 mL). After stirring for 24 hours at room temperature, concentrated HCl (10.9 g) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 31.0 g.

Example 54

Polyethylenimine, 80% ethoxylated

A solution of polyethylenimine, 80 percent ethoxylated (269.1 g of a 35–40 percent solution in water; Aldrich Chemical Company) was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford the desired compound.

Example 55

Copoly(N-[3-(dimethylamino)propyl]acrylamide/ acrylamide/N-dodecylacrylamide) (48:48:5).

A solution of N-[3-(dimethylamino)propyl]acrylamide (30.0 g), acrylamide (13.6 g), and N-dodecylacrylamide (4.6 g) in deionized water (50 mL) and ethanol (50 mL) was heated to 60° C. under a nitrogen atmosphere. When the solution reached 60° C., 2,2'-azobis(2-amidinopropane) dihydrochloride (2.4 g of a 20 percent aqueous solution) was added. Heating was continued for 18 hours under a nitrogen atmosphere. After cooling to room temperature, the reaction solution was dissolved in isopropanol (150 mL), and concentrated HCl (29.5 g) was added with stirring. The solution was decanted from the precipitated polymer. The polymer was suspended in isopropanol (500 mL), stirred for at least 15 minutes, and allowed to settle. After decanting, the polymer was similarly washed an additional 3 times with isopropanol. The washed polymer was dried in a forced-air oven at 70° C. to afford 81.1 g.

Example 56

Copoly(N-[3-(dimethylamino)propyl]acrylamide/ acrylamide) (50/50)

A solution of N-[3-(dimethylamino)propyl]acrylamide (30.0 g) and acrylamide (13.6 g) in deionized water (40 mL) and ethanol (40 mL) was heated to 60° C. under a nitrogen atmosphere. When the solution reached 60° C., 2,2'-azobis (2-amidinopropane) dihydrochloride (2.2 g of a 20 percent aqueous solution) was added. Heating was continued for 18 hours under a nitrogen atmosphere. After cooling to room temperature, the reaction solution was dissolved in isopropanol (150 mL), and concentrated HCl (31.5 g) was added with stirring. The solution was decanted from the precipitated polymer. The polymer was suspended in isopropanol (500 mL), stirred for at least 15 minutes, and allowed to settle. After decanting, the polymer was similarly washed an additional 3 times with isopropanol. The washed polymer was dried in a forced-air oven at 70° C. to afford 68.2 g.

Example 57

Copoly(N-[3-(dimethylamino)propyl]acrylamide/ acrylamide/N-dodecylacrylamide) (75/20/5)

A solution of N-[3-(dimethylamino)propyl]acrylamide (22.5 g), acrylamide (2.7 g), and N-dodecylacrylamide (2.3 g) in deionized water (30 mL) and ethanol (30 mL) was heated to 60° C. under a nitrogen atmosphere. When the solution reached 60° C., 2,2'-azobis(2-amidinopropane) dihydrochloride (1.4 g of a 20 percent aqueous solution) was added. Heating was continued for 18 hours under a nitrogen atmosphere. After cooling to room temperature, the reaction solution was dissolved in isopropanol (150 mL), and concentrated HCl (29.2 g) was added with stirring. The solution was decanted from the precipitated polymer. The polymer was suspended in isopropanol (500 mL), stirred for at least 15 minutes, and allowed to settle. After decanting, the polymer was similarly washed an additional 3 times with isopropanol. The washed polymer was dried in a forced-air oven at 70° C. to afford 34.7 g.

Example 58

Functionalization of polydiallylamine with (6-bromohexyl) trimethylammonium bromide A solution of polydiallylamine hydrochloride (106.8 g of a 28.09 percent aqueous solution), deionized water (400 g), NaOH (9.6 g of a 50 percent aqueous solution), and (6-bromohexyl) trimethylammonium bromide (51.1 g) was heated to 60° C. for 18 hours. After 1 hour at 60° C., NaOH (4.5 g of a 50 percent aqueous solution) was added. After 1.5 hours at 60° C., NaOH (4.5 g of a 50 percent aqueous solution) was added. After 2 hours at 60° C., NaOH (4.5 g of a 50 percent aqueous solution) was added. Concentrated HCl was added until the reaction solution had a pH <1. The solution was then poured into isopropanol (4 L) and stirred for at least 15 minutes. The solution was decanted from the precipitated polymer. The polymer was suspended in isopropanol (4 L), stirred for at least 15 minutes, and allowed to settle. After decanting, the polymer was similarly washed an additional time with isopropanol. The washed polymer was dried in a forced-air oven at 70° C. to afford 69.4 g.

Example 59

Functionalization of poly(diallylmethylamine) with poly(ethylene glycol) diglycidyl ether A basic solution of polydiallylmethylamine was prepared by mixing polydiallylmethylamine hydrochloride (615.4 g of a 44.22 percent aqueous solution), deionized water (745.2 g) and NaOH (78.0 g of a 50 percent aqueous solution) overnight. To a portion of the polydiallylmethylamine basic solution (158.6 g) was added poly(ethylene glycol) diglycidyl ether (9.0 g, Average Mn ca. 526, from Aldrich Chemical Co.). After stirring overnight, concentrated HCl (10 mL) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 9.3 g.

Example 60

Poly[bis(2-chloroethyl)ether-alt-1,3-bis[3-(dimethylamino)propyl]urea], quaternized A solution of poly[bis(2-chloroethyl)ether-alt-1,3-bis[3-(dimethylamino)propyl]urea], quaternized (566.7 g of a 62 percent solution in water; from Aldrich Chemical Co.) was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford the desired compound.

Example 61

Functionalization of polyethylenimine with glycidol

A solution of polyethylenimine (60.0 g), deionized water (240 g), and glycidol (46.2 mL) was heated at 50° C. under a nitrogen atmosphere for 18 hours. After cooling to room temperature, concentrated HCl (50 mL) was added. The reaction was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford the desired compound.

Example 62

Functionalization of polyethylenimine with 2-bromoethanol

A solution of polyethylenimine (60.0 g), deionized water (240 g), and 2-bromoethanol (49.4 mL) was heated at 50° C. under a nitrogen atmosphere for 18 hours. After 1.5 hours at 50° C., NaOH (31.9 g of a 50 percent aqueous solution) was added. After cooling to room temperature, concentrated HCl (30 mL) was added. The reaction mixture was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford the desired compound.

Example 63

Protonation of polydiallylmethylamine with L-tartaric acid

A basic solution of polydiallylmethylamine was prepared by mixing polydiallylmethylamine hydrochloride (615.4 g of a 44.22 percent aqueous solution), deionized water (745.2 g) and NaOH (78.0 g of a 50 percent aqueous solution) overnight.

To a portion of the polydiallylmethylamine basic solution (158.6 g) was added L-tartaric acid (30.8 g). After stirring overnight, the solution was poured into isopropanol (3 L) and stirred for at least 15 minutes. The solution was decanted from the precipitated polymer. The polymer was suspended in isopropanol (3 L), stirred for at least 15 minutes, and allowed to settle. After decanting, the polymer was similarly washed an additional time with isopropanol. The washed polymer was dried in a forced-air oven at 70° C. to afford 45.2 g.

Example 64

Polydiallyldimethylammonium chloride

Polydiallyldimethylammonium chloride (526.8 g of a 20 percent aqueous solution, average MW 200,000–350,000, from Aldrich Chemical Co.) was poured into isopropanol (12 L) and stirred for at least 15 minutes. The solution was decanted from the precipitated polymer. The washed polymer was dried in a forced-air oven at 70° C. to afford 90.8 g.

Example 65

Functionalization of poly(diallylmethylamine) with polyoxyethylene(2,000) Methyl Glycidyl Ether NaH (3.28 g; 60 percent in oil from VWR) was weighed out in a three-necked 1-L round-bottomed flask and washed 3 times with 200 mL of hexane. The hexane was removed and the NaH was suspended in 350 mL of anhydrous dioxane. Polyoxyethylene(2,000) methyl glycidyl ether (130 g; average Mn 2,000, obtained from Aldrich Chemical Co.) was dissolved in 250 mL of dioxane and then added to the above stirred solution at room temperature under a nitrogen atmosphere. The solution was stirred for a further hour at room temperature. The reaction mixture was heated to 45° C. and then 12.03 g of epichlorohydrin was added to this solution and the reaction mixture was heated overnight. The reaction was allowed to cool to room temperature and was then filtered. The filtered solution was concentrated using a rotary evaporator to give a white solid. The solid was dissolved in 500 mL of methylene chloride and the polymer was precipitated in 4 L of diethyl ether. The polymer was dissolved in 500 ml, of methylene chloride and the polymer was precipitated in 4 L of diethyl ether and filtered. The polymer was dried in a vacuum oven at room temperature over 72 hours to afford 110.9 g of polyoxyethylene (2,000) methyl glycidyl ether.

A solution of polydiallylmethylamine hydrochloride (67.7 g of a 44.22 percent aqueous solution), deionized water (82.3 g) and NaOH (8.7 g of a 50 percent aqueous solution) was heated at 60° C. for 3.5 hours. Polyoxyethylene (2,000) methyl glycidyl ether (1.5 g) was then added and the solution was heated at 60° C. for an additional 8 hours. After cooling to room temperature, the reaction mixture was poured into acetone (4 L) and stirred for at least 15 minutes. The solution was decanted from the precipitated polymer. The polymer was suspended in acetone (2 L), stirred for at least 15 minutes, and allowed to settle. After decanting, the polymer was similarly washed an additional time with acetone. The washed polymer was dried in a forced-air oven at 70° C. to afford 26.4 g.

No Example 66

Example 67

Functionalization of poly(diallylmethylamine) with polyoxyethylene(2,000) methyl glycidyl ether A solution of polydiallylmethylamine hydrochloride (67.7 g of a 44.22 percent aqueous solution), deionized water (82.3 g) and NaOH (8.7 g of a 50 percent aqueous solution) was heated at 60° C. for 3.5 hours. Polyoxyethylene(2,000) methyl glycidyl ether (3.0 g) was then added and the solution was heated at 60° C. for an additional 8 hours. After cooling to room temperature, the reaction mixture was poured into acetone (4 L) and stirred for at least 15 minutes. The solution was decanted from the precipitated polymer. The polymer was suspended in acetone (2 L), stirred for at least 15 minutes, and allowed to settle. After decanting, the polymer was similarly washed an additional time with acetone. The washed polymer was dried in a forced-air oven at 70° C. to afford 23.2 g.

Example 68

Copoly(diallylmethylamine/acrylamide) (50:50).

A solution of diallylmethylammonium chloride was prepared by adding diallylmethylamine (250 g) dropwise to a solution that was cooled in an ice-water bath to 10° C., of deionized water (192.3 g) and concentrated HCl (222.2 g). A solution of diallylmethylammonium chloride (59.1 g of the 50 percent aqueous solution), acrylamide (14.2 g), and 2,2'-azobis(2-amidinopropane) dihydrochloride (2.7 g of a 20 percent aqueous solution) in deionized water (14.2 g) was heated to 60° C. for 18 hours under a nitrogen atmosphere. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 25.2 g.

Example 69

Copoly(diallyldimethylammonium chloride/acrylamide) (50:50).

A solution of diallyldimethylammonium chloride (49.8 g of a 65 percent solution in water), acrylamide (14.2 g), and 2,2'-azobis(2-amidinopropane) dihydrochloride (2.7 g of a 20 percent aqueous solution) in deionized water (91.1 g) was heated to 60° C. for 18 hours under a nitrogen atmosphere. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 27.8 g.

Example 70

Functionalization of polydiallylmethylamine with epichlorohydrin

To a solution of polydiallylmethylammonium hydrochloride (67.8 g of a 44.22 percent aqueous solution), deionized water (82.8 g), and NaOH (8.7 g of a 50 percent aqueous solution) was added epichlorohydrin (0.159 mL). The reaction was heated under a nitrogen atmosphere at 45° C. overnight. After 30 minutes of heating, the solution gelled. After the heating period, the reaction was allowed to cool to room temperature, and concentrated HCl (10.9 g) and deionized water (250 mL) were added. The resulting slurry was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 26.8 g.

Example 71

Copoly(diallyldimethylammonium Chloride/poly(ethylene Glycol) Methyl Ether Acrylate)

A solution of diallyldimethylammonium chloride (41.5 g of a 65 percent solution in water), poly(ethylene glycol) methyl ether acrylate (3.0 g, Average Mn 454, obtained from Aldrich Chemical Co.), and 2,2'-azobis(2-amidinopropane) dihydrochloride (0.3 g) in 2-methyl-2-propanol (60 g) and deionized water (60 g) was heated to 60° C. for 16.5 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), stirred for at least 15 minutes, and allowed to settle. The washed polymer was dried in a forced-air oven at 70° C. to afford 16.3 g.

Example 72

Copoly(diallyldimethylammonium Chloride/poly(propylene Glycol) Methyl Ether Acrylate)

A solution of diallyldimethylammonium chloride (41.5 g of a 65 percent solution in water), poly(propylene glycol) methyl ether acrylate (3.0 g, Average Mn 202, obtained from Aldrich Chemical Co.), and 2,2'-azobis(2-amidinopropane) dihydrochloride (0.3 g) in 2-methyl-2-propanol (60 g) and deionized water (60 g) was heated to 60° C. for 16.5 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), stirred for at least 15 minutes, and allowed to settle. The washed polymer was dried in a forced-air oven at 70° C. to afford 18.2 g.

Example 73

Copoly(diallyldimethylammonium chloride/vinyl alcohol) (50:50).

A solution of diallyldimethylammonium chloride (32.6 g of a 65 percent solution in water), vinyl acetate (10.53 g), and 2,2'-azobis(2-amidinopropane) dihydrochloride (0.64 g) in 2-methyl-2-propanol (60 g) and deionized water (60 g) was heated to 60° C. for 21 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), stirred for at least 15 minutes, and allowed to settle. The washed polymer was dried in a forced-air oven at 70° C. to afford 11.5 g. To a solution of a portion of the washed polymer (5.5 g) in deionized water (100 mL) was added NaOH (0.15 g of a 50 percent aqueous solution). The solution was heated at 60° C. with stirring for 23.5 hours. The reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 4.5 g.

Example 74

Copoly(diallyldimethylammonium Chloride/poly(ethylene glycol acrylate)

A solution of diallyldimethylammonium chloride (36.9 g of a 65 percent solution in water), poly(ethylene glycol) methyl ether acrylate (6.0 g, Average Mn 375, obtained from Aldrich Chemical Co.), and 2,2'-azobis(2-amidinopropane) dihydrochloride (0.3 g) in deionized water (120 g) was heated to 60° C. for 18 hours under a nitrogen atmosphere. After cooling to room temperature, the reaction solution was poured into acetone (2 L) and stirred for at least 15 minutes. The solution was decanted from the precipitated polymer. The polymer was suspended in acetone (2 L), stirred for at least 15 minutes, and allowed to settle. After decanting, the polymer was suspended in acetone (2 L), stirred for at least 15 minutes, and allowed to settle. The washed polymer was dried in a forced-air oven at 70° C. to afford 20.0 g.

Example 75

Copoly(diallyldimethylammonium chloride/acrylic acid) (90:10).

A solution of diallyldimethylammonium chloride (73.29 g of a 65 percent solution in water), acrylic acid (2.36 g) and 2,2'-azobis(2-amidinopropane) dihydrochloride (0.444 g) in deionized water (175 mL) was heated to 60° C. for 18 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), ground in a blender for at least 5 minutes, stirred for at least 15 minutes, and allowed to settle. The washed polymer was dried in a forced-air oven at 70° C. to afford 35.0 g.

Example 76

Copoly(diallyldimethylammonium chloride/acrylic acid) (75:25).

A solution of diallyldimethylammonium chloride (66.97 g of a 65 percent solution in water), acrylic acid (6.47 g) and 2,2'-azobis(2-amidinopropane) dihydrochloride (0.487 g) in deionized water (175 mL) was heated to 60° C. for 18 hours under a nitrogen atmosphere. After cooling to room temperature, the reaction solution was poured into isopropanol (2 L) and stirred for at least 15 minutes. The solution was

Example 77

Functionalization of poly(diallylmethylamine) with 3-bromopropionic acid

A basic solution of polydiallylmethylamine was prepared by mixing polydiallylmethylamine hydrochloride (615.4 g of a 44.22 percent aqueous solution), deionized water (745.2 g) and NaOH (78.0 g of a 50 percent aqueous solution) overnight.

To a portion of the basic solution of polydiallylmethylamine (158.6 g) was added deionized water (141.4 g) and 3-bromopropionic acid (15.5 g). This solution was heated to 50° C., and then NaOH (16.2 g of a 50 percent aqueous solution) was added. The reaction solution was heated at 50° C. for 18.5 hours. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 29.2 g.

Example 78

Functionalization of poly(diallylmethylamine) with 4-bromobutyric Acid

To a portion of the basic solution of polydiallylmethylamine (158.6 g; Example 77) was added deionized water (141.4 g) and 3-bromobutyric acid (17.0 g). This solution was heated to 50° C., and then NaOH (16.2 g of a 50 percent aqueous solution) was added. The reaction solution was heated at 50° C. for 18.5 hours. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 20.0 g.

Example 79

Functionalization of poly(diallylmethylamine) with 2-bromoethanesulfonic acid

To a portion of the basic solution of polydiallylmethylamine (158.6 g; Example 77) was added deionized water (141.4 g) and 2-bromoethanesulfonic acid (21.4 g). This solution was heated to 50° C., and then NaOH (16.2 g of a 50 percent aqueous solution) was added. The reaction solution was heated at 50° C. for 19 hours. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 28.8 g.

Example 80

Functionalization of poly(diallylmethylamine) with 1,3-propane sultone

To a portion of the basic solution of polydiallylmethylamine (158.6 g; Example 77) was added deionized water (141.4 g) and 1,3-propane sultone (12.4 g). This solution was heated to 50° C., and then NaOH (16.2 g of a 50 percent aqueous solution) was added. The reaction solution was heated at 50° C. for 19 hours. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), ground in a blender for at least 5 minutes, stirred for at least 15 minutes, and allowed to settle. The washed polymer was dried in a forced-air oven at 70° C. to afford 38.8 g.

Example 81

Functionalization of poly(diallylmethylamine) with 2-bromoethanol

To a portion of the basic solution of polydiallylmethylamine (158.6 g; Example 77) was added deionized water (150 mL) and 2-bromoethanol (40.06 g). This solution was heated to 45° C., and then NaOH (16.2 g of a 50 percent aqueous solution) was added. The reaction solution was heated at 45° C. for 21 hours. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 40.2 g.

Example 82

Functionalization of poly(diallylamine) with 2-bromoethanol

A basic solution of polydiallylamine was prepared by mixing polydiallylamine hydrochloride (519.03 g of a 28.9 percent aqueous solution), deionized water (230.97 g) and NaOH (48.0 g of a 50 percent aqueous solution) overnight.

To a portion of the polydiallylamine basic solution (133.62 g) was added 2-bromoethanol (65.77 g). This solution was heated to 45° C., and then NaOH (16.2 g of a 50 percent aqueous solution) was added. The reaction solution was heated at 45° C. for 18 hours. After 3 hours at 45° C., NaOH (50 percent aqueous solution) was added to bring the pH from 8.5 to 9.6. After cooling to room temperature, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 41.0 g.

decanted from the precipitated polymer. The polymer was suspended in isopropanol (2 L), stirred for at least 15 minutes, and allowed to settle. After decanting, the polymer was suspended in isopropanol (2 L), ground in a blender for at least 5 minutes, stirred for at least 15 minutes, and allowed to settle. The washed polymer was dried in a forced-air oven at 70° C. to afford 38.9 g.

Example 83

Copoly[(3-acrylamidopropyl)trimethylammonium chloride]/acrylic acid](90:10).

A solution of (3-acrylamidopropyl)trimethylammonium chloride (64.2 g of a 75 percent solution in water), acrylic acid (1.86 g) and 2,2'-azobis(2-amidinopropane) dihydrochloride (0.351 g) in deionized water (190 mL) was heated to 60° C. for 8 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), stirred for at least 15 minutes, and allowed to settle. The washed polymer was dried in a forced-air oven at 70° C. to afford 44.8 g.

Example 84

Copoly[(3-acrylamidopropyl)trimethylammonium chloride]/acrylic acid](75:25).

A solution of (3-acrylamidopropyl)trimethylammonium chloride (59.7 g of a 75 percent solution in water), acrylic acid (5.21 g) and 2,2'-azobis(2-amidinopropane) dihydrochloride (0.392 g) in deionized water (190 mL) was heated to 60° C. for 8 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), stirred for at least 15 minutes, and allowed to settle. The washed polymer was dried in a forced-air oven at 70° C. to afford 47.1 g.

Example 85

Copoly(diallyldimethylammonium chloride/poly(ethylene glycol) methyl ether acrylate)

A solution of diallyldimethylammonium chloride (50.0 g of a 50 percent solution in water), poly(ethylene glycol) methyl ether acrylate (25.0 g, Average Mn 454, obtained from Aldrich Chemical Co.), and 2,2'-azobis(2-amidinopropane) dihydrochloride (0.5 g) in deionized water (190 mL) was heated to 60° C. for 16 hours under a nitrogen atmosphere. After cooling to room temperature, deionized water (200 mL) was added and after thoroughly mixing, the reaction solution was transferred to a Spectra/Por 1 dialysis membrane bag (molecular weight cutoff 6000 to 8000) and dialyzed against deionized water for at least 18 hours. The dialyzed polymer solution was dried in a forced-air oven at 70° C. to afford 31.0 g.

Example 86

Copoly[(3-acrylamidopropyl)trimethylammonium chloride/poly(ethylene glycol) methyl ether acrylate]

A solution of poly(ethylene glycol) methyl ether (10.0 g, Average Mn 2,000, obtained from Aldrich Chemical Co.), triethylamine (5.06 g), and 3,5-di-tert-butyl-4-hydroxyanisole (0.06 g) in tetrahydrofuran (250 mL) was cooled in an ice-water bath. While maintaining the temperature of the reaction solution at 5–15° C., a solution of acryloyl chloride (4.53 g) in tetrahydrofuran (30 mL) was added slowly. Following the addition, the reaction solution was heated at 40° C. for 24 hours and then stored at 4° C. for 72 hours. The upper liquid layer was decanted from the precipitate, and concentrated on a rotary evaporator to remove most of the tetrahydrofuran. The concentrated solution was then poured into diethyl ether, and the light yellow precipitate was filtered and dried under vacuum to afford 2.5 g of solid poly(ethylene glycol) methyl ether acrylate. Additional material was isolated from the initial precipitate by mixing it with tetrahydrofuran (250 mL) and heating at 35° C. for 2 hours. The mixture was filtered through celite, and the filtered solution was concentrated on a rotary evaporator to remove most of the tetrahydrofuran. The concentrated solution was poured into diethyl ether, and the light yellow precipitate was filtered and dried under vacuum to afford 3.2 g of solid poly(ethylene glycol) methyl ether acrylate.

A solution of (3-acrylamidopropyl)trimethylammonium chloride (18.0 g of a 75 percent solution in water), poly(ethylene glycol) methyl ether acrylate (1.5 g), and 2,2'-azobis(2-amidinopropane) dihydrochloride (0.15 g) in deionized water (60.0 g) was heated to 60° C. for 4 hours under a nitrogen atmosphere. After cooling to room temperature, the reaction solution was poured into isopropanol (2 L) and stirred for at least 15 minutes. The solution was decanted from the precipitated polymer. The polymer was suspended in isopropanol (2 L), stirred for at least 15 minutes, and allowed to settle. After decanting, the polymer was suspended in isopropanol (2 L), stirred for at least 15 minutes, and allowed to settle. The washed polymer was dried in a forced-air oven at 70° C. to afford 14.5 g.

Example 87

Preparation of a copolymer of diallyamine HCL (50% and acylamide (50%)

Diallylamine (60 g, 617 mmole) was suspended in water (200 mL) which was acidified with concentrated HCl to pH 1.5 at 10–15° C. Acrylamide (43.85 g, 617 mmol) was added and the reaction mixture was purged with nitrogen for 10 minutes, followed by the addition of 2,2'-azobisisobutyronitrile (500 mg). The reaction mixture was slowly heated to 65° C. and the heating was continued for 16 hours under nitrogen. The reaction contents were poured into isopropanol (2 L) and the polymer precipitated. The supernatant was removed and replaced with fresh isopropanol (2 L). This process was repeated 2 more times. The polymer was finally collected by filtration and the material was dried under vacuum at 45° C. The polymer was ground, passed through an 80 mesh sieve, and dried again in a vacuum oven to yield 100 g of product.

Example 88

Preparation of a copolymer of (3-acrylamidopropyl) trimethylammonium choloride (75 mole %) and acrylamide (25 mole %)

A 30-L reaction vessel was charged with (3-acrylamidopropyl) trimethylammonium chloride (2481 g of 50 percent solution, 6 moles) and acrylamide (142.16 g, 2 moles). Isopropanol (6 L) was added and the vessel was purged with nitrogen for 10 minutes prior to the addition of 2,2'-azobisisobutyronitrile (5.28 g). The reaction mixture was heated to 70° C. for 21 hours under nitrogen. The reaction mixture was collected in a bucket, the supernatant was decanted, and the material was suspended in boiling isopropanol (3 L). The mixture was stirred with overhead stirrer for 20 minutes. The solvent was replaced with fresh boiling isopropanol (3 L) and the process was repeated 3 more times. Finally the material was suspended in isopropanol (4 L) at room temperature for 1 day. The polymer became slightly brittle and was ground in a blender. The polymer was collected by filtration and washed with isopropanol (2×3 L). The polymer was dried under vacuum at 60° C. for 2 days. The polymer was ground and passed through an 80 mesh sieve to yield 1260 g of product.

Example 89

Preparation of a copolymer of (3-acrylamidopropyl) trimethylammonium chloride (75 mole %), crylamide (20 mole %) and N-octoylacrylamide (5 mole %)

A three-necked round-bottomed flask (1 L) was charged with (3-acrylamidopropyl) trimethylammonium chloride (62 g of 50 percent solution, 150 mmol), acrylamide (2.84 g, 40 mmol), octylacrylamide (1.83 g, 10 mmol) and isopropanol 160 mL. The mixture was purged with nitrogen for 10 minutes prior to the addition of 2,2'azobisisobutyronitrile (132 mg). The reaction mixture was heated to 70° C. for 16 hours. At the end of reaction, the solvent was removed from the reaction mixture and the precipitated polymer was poured into boiling isopropanol (1 L). The solvent was replaced with fresh boiling isopropanol. The process was repeated 3 more times. Finally, the polymer was suspended in isopropanol (1 L) at room temperature for 6 hours. The polymer was collected and dried under vacuum at 60° C. The polymer was ground and passed through an 80 mesh sieve to yield 30 g of product.

Example 90

Preparation of the methylenebisacrylamide (1 mole %) Cross-linked copolymer of (3-acrylamidopropyl) trimethylammonium choloride (75%)), acrylamide (20 mole %) and N-dodecylacrylamide (5 mole %)

A three-necked round-bottomed flask (1 L) was charged with (3-acrylamidopropyl) trimethylammonium chloride (124 g of 50 percent solution, 300 mmole), acrylamide (5.68 g, 80 mmole), dodecylacrylamide (4.78 g, 20 mmole) and methylenebisacrylamide (616.7 mg, 4 mmole). Water (80 mL) and ethanol 80 mL were added. The mixture was purged with nitrogen for 10 minutes prior to the addition of 2,2'-azobis (2-amidinopropane) dihydrochloride (400 mg). The reaction mixture was heated to 65° C. for 16 hours. The reaction was gelled within 2 hours. At the end of reaction, the solvent was removed from the reaction mixture. The precipitated polymer gel was suspended in boiling isopropanol (1 L). The solvent was replaced with fresh boiling isopropanol. The process was repeated 3 more times. Finally, the polymer was suspended in isopropanol (1 L) and ground in a blender. The polymer was collected and dried under vacuum at 60° C. The polymer powdered, suspended in water (2.5 L), and filtered. The gel was washed with water (4×2.5 L) followed by isopropanol (3×4 L). The polymer was dried in a vacuum oven to yield 60 g of product.

Example 91

Preparation of poly[(n-vinylimidazole-co-(1-vinyl-3-methylimidazole-co-(1-vinyl-3-dodecylimidazole)] 20/75/5

To a 5 liter flask with mechanical stirrer, nitrogen purge, and temperature controller was added: n-vinylimidazole (500 g; 5.31 moles), deionized water (250 mL), and enough HCl to make the pH=0.8 (approximately 500 mL of 37 percent solution). Enough water was added to make the reaction solution 25 percent solids and this was degassed via nitrogen purge for 1 hour. The reaction was heated to 60° C. at which point was added 2,2'-azobis (2-amidinopropane) dihydrochloride (2.5 g) dissolved in 2 mL of water. A small exotherm of 7° C. was noted and after 105 minutes an additional charge of 2,2'-azobis (2-amidinopropane) dihydrochloride (2.5 g of) in 2 mL of water was added. Total heating time at 60° C. was 8 hours. After the reaction was cooled to room temperature, the pH was adjusted to 13.2 with aqueous sodium hydroxide and the clear liquid was poured away from the gummy solid. The gummy solid was taken up in enough deionized water to make 12 percent of n-vinylimidazole homopolymer.

To a 1 liter flask with mechanical stirrer and temperature controller was added: 300 g n-vinylimidazole homopolymer solution and enough concentrated HCl to make the pH=8.25. To this was added 4.768 g dodecyl bromide (0.0191 moles) and the reaction mixture was heated to 80° C. for 20 hours (the solution became cloudy after a few minutes). The reaction was allowed to cool to 40° C. and dimethyl sulfate was added in 5 mL portions (0.287 moles total). NaOH (5 mL of 50 percent) was added and the reaction mixture was allowed to stir at room temperature for 20 hours (pH ~13.5). The reaction mixture was heated to 45° C. for 3 hours to kill any unreacted dimethyl sulfate. The pH was adjusted to 1.2 with HCl and the mixture was triterated into isopropanol. The liquid was poured off, the polymer was re-dissolved in deionized water and re-triterated into isopropanol. The polymer was dissolved in 300 mL of deionized water and 125 mL of Amberlite Cl-ion exchange resin beads for 4 hours. The polymer was filtered off, the beads were rinsed with water and the polymer solution was allowed to dry in a convection oven at 60° C. to yield 51.2 g of solid.

Example 92

Preparation of Poly[(diallyl dimethyl ammonium chloride)-co-(n-vinyl glycine)] 70/30

To a 500-mL flask with mechanical stirrer, nitrogen purge, and temperature controller was added: diallyldimethyl ammonium chloride (66.85 g of 65 percent solution in water, 43.45 g solids, 0.2687 moles), allylamine HCl (24.12 g of 27.16 percent solution based on allylamine charged in water, 0.1149 moles), and deionized water (75.69 mL) to make 30 percent solids (based on un-protonated monomers charged). The reaction mixture was degassed via nitrogen purge for 1 hour and then heated to 60° C. at which time 2,2'-azobis (2-amidinopropane) dihydrochloride (0.25 g) in ~1 mL of water was added. This was followed 30 minutes later with an additional charge of 2,2'-azobis (2-amidinopropane) dihydrochloride (0.25 g in ~1 mL of water). Further additional charges were made at 5 hours, 20 hours, and 28 hours. At 48 hours the temperature was raised to 80° C. for 1 hour and then turned off and the reaction was allowed to cool to room temperature. To this polymer solution was added chloroacetic acid (10.846 g; 0.1149 moles) and the pH was adjusted to 10 with 50 percent NaOH solution in water. This mixture was heated at 40° C. for 24 hours. The heat was then turned off and the polymer was triterated into acetone. The liquid was poured off and the polymer was re-dissolved into deionized water, the pH adjusted to ~2 with HCl (37 percent) and triterated again into acetone. The polymer was dissolved into deionized water once more and triterated into acetone. The polymer was then dissolved into water and placed in a 60° C. convection oven to dry to 55.1 g of amber glassy solid.

Example 93

Preparation of Poly[(diallyl dimethyl ammonium chloride)-co-(n-allyl pentylamine)-co-(n-allyl glycine)

To a 500-mL flask with mechanical stirrer, nitrogen purge, and temperature controller was added: diallyldimethylammonium chloride (891 g of 65 percent solution in water; 579.15 g solids; 3.58 moles), allylamine HCl (321.5 g of 27.16 percent solution based on allylamine charged in water, 1.53 moles), and deionized water (454 mL) to make 40 percent solids (based on un-protonated monomers charged). The reaction mixture was degassed via nitrogen purge for 1 hour and then heated to 60° C. at which time 1.67 g of 2,2'-azobis (2-amidinopropane) dihydrochloride in ~2 mL of water was added. This was followed 15 minutes later with an additional charge of 2,2'-azobis (2-amidinopropane) dihydrochloride (1.67 g). Additional charges were made at 16 hours, and 24 hours. At 40 hours the temperature was raised to 80° C. for 1 hour and then turned off and the reaction was allowed to cool to room temperature.

To a 500 mL flask with mechanical stirrer and temperature controller was added: 250 g of the reaction mixture above (40 percent, 100 g solids based on un-protonated monomers charged). The pH was adjusted to 10 with 50 percent NaOH in water. The temperature was raised to 70° C. and the reaction was subsequently charged with n-chlorodecane (9.32 mL; 0.046 moles) and allowed to stir for 20 hours. The reaction was allowed to cool to room temperature before adding chloroacetic acid (30 g; 0.3177 moles) and the pH was readjusted to 10. The reaction was allowed to stir at 40° C. for 20 hours. The polymer was then precipitated into acetone and the liquid was decanted. The polymer was redissolved in deionized water and re-triterated into acetone; this procedure was repeated once more. The polymer was then dissolved in deionized water and the pH was adjusted to ~2 with HCl (37 percent) and the triteration into acetone procedure was repeated three more times. The polymer was dissolved in water and placed in a convection oven at 60° C. to dry to 36.9 g of glassy solid.

No Example 94

Example 95

Preparation of poly[((3-acrylamidopropyl) trimethylammonium chloride)-co-(acrylamide)-co-(n-octadecylacrylamide)] 60/35/5

To a 500-mL flask with mechanical stirrer, temperature controller, and nitrogen purge was added: (3-acrylamidopropyl) trimethylammonium chloride (25.04 g of 75 percent in water; 18.78 g solids; 0.091 moles), acrylamide (3.77 g; 0.053 moles), n-octadecylacrylamide (2.45 g; 0.0076 moles), deionized water (12.52 mL), and isopropanol (121 mL). This mixture was degassed for 1 hour prior to heating to 70° C. 2,2'-Azobisisobutyronitrile (0.1 g) was added when the temperature reached 62° C. and all of the reactants were dissolved. The reaction was allowed to heat with stirring and nitrogen purge for 4 hours. Isopropanol (200 mL) was added to the flask and the heat was turned off. The precipitated polymer was stirred in the hot isopropanol for ten minutes before pouring off the liquid. The polymer was scraped out of the flask and dried in a 60° C. convection oven to yield 21.2 g of solid.

Example 96

Preparation of poly[(diallyl ammonium choloride)-co-(acrylamide)] 25/75

To a 500-mL flask with mechanical stirrer, temperature controller, and nitrogen purge was added: diallylamine (8.88 g; 0.092 moles), and deionized water (20 mL). The mixture was cooled in an ice bath and 50 percent concentrated HCL in water was slowly added dropwise until the pH reached 0.86. Acrylamide (19.49 g; 0.2749 moles), 2,2'-azobis (2-amidinopropane) dihydrochloride (0.31 g), and deionized water (20 mL) were added. The reaction mixture was degassed with nitrogen for 30 minutes and the temperature was raised to 55° C. at which point the flask was placed in an ice bath to control the exotherm (maximum temperature 78° C.). The temperature was maintained at 60° C. for 4 hours. The polymer was precipitated into acetone and washed twice with more acetone. The polymer was dried in a 70° C. convection oven to yield 25.1 g of solid.

Example 97

Preparation of poly[(diallyl ammonium chloride)-co-(acrylamide)] 75/25

To a 500-mL flask with mechanical stirrer, temperature controller, and nitrogen purge was added: diallylamine (20.69 g; 0.213 moles), and deionized water (20 mL). The mixture was cooled in an ice bath and 50 percent concentrated HCL in water was added dropwise until the pH reached 0.9. Acrylamide (5.05 g; 0.0711 moles), 2,2'-azobis (2-amidinopropane) dihydrochloride (0.335 g), and deionized water (20 mL) were added. The reaction mixture was degassed with nitrogen for 30 minutes and the temperature was raised to 65° C. An additional charge of 2,2'-azobis (2-amidinopropane) dihydrochloride (0.335 g) was made at 24 hours and another at 48 hours. At 72 hours the polymer was precipitated into acetone and washed twice with more acetone. The polymer was dried in a 70° C. convection oven to yield 24.6 g of solid.

Example 98

Preparation of poly[((3-acrylamidopropyl) trimethylammonium chloride)-co-(acrylamide)-co-(n-octadecylacrylamide)] 50/45/5

To a 500-mL flask with mechanical stirrer, temperature controller, and nitrogen purge was added: (3-acrylamidopropyl) trimethylammonium chloride (22.7 g of 75 percent in water; 17.0 g solids), acrylamide (5.3 g), n-octadecylacrylamide (2.7 g), deionized water (11.4 mL), and isopropanol (132 mL). This mixture was degassed for 1 hour prior to heating to 70° C. 2,2'-Azobisisobutyronitrile (0.11 g) was added when the temperature reached 62° C. and all of the reactants were dissolved. The reaction was allowed to heat with stirring and nitrogen purge for 4 hours. Isopropanol (200 mL) was added to the flask and the heat was turned off. The precipitated polymer was stirred in the hot isopropanol for ten minutes before pouring off the liquid. The polymer was scraped out of the flask and dried in a 60° C. convection oven to yield 18.3 g of solid.

Fat-Binding Evaluation via Paper Staining

The model consists of male, Sprague Dawly rats, 160 g, housed individually in wire mesh cages. They were acclimated to the facility for six days, during which time they were fed a chow based diet supplemented with 15 percent lard by weight. Feed and water were provided ad libitum. The animals were then randomly assigned to groups of four and fed test diets for three days. The test diet was also a chow based feed. A lipase inhibitor (Orlistat) was added at 0.04 percent by weight and the polymer was added at 0.30 percent by weight. They were mixed in the feed as a powder followed by the addition of the supplemented fat in the form of lard at 15 percent by weight. During the final 24 hours of the treatment period an 8.5"×11" sheet of white paper was placed beneath each cage. One inch squares were drawn on the paper creating a grid of 80 squares. When oil in the form of unabsorbed dietary triglyceride seeps from the stool, it stains the paper. This can be readily discerned from urine if the papers were allowed to dry for six hours. The oil stains confer translucence to the paper. The squares that contain these oil stains were counted and expressed as a percentage of total area stained.

Some of the examples described above were tested in this model, and the following results were obtained:

| Test Polymer | Percentage of Paper Stained |
|---|---|
| Control 1: no lipase inhibitor no polymer | 0 |
| Control 2: no polymer | 39 ± 6 (average of 24 experiments) |
| Example | |
| 1 | 9 |
| 2 | 17 |
| 3 | 8 |
| 4 | 9 |
| 5 | 7 |
| 6 | 10 |
| 7 | 7 |
| 8 | 13 |
| 9 | 11 |
| 10 | 11 |
| 11 | 19 |
| 12 | 7 |
| 13 | 11 |
| 14 | 12 |
| 15 | 7 |
| 16 | 8 |
| 17 | 4 |
| 18 | 7 |
| 19 | 4 |
| 20 | 7 |
| 21 | 9 |
| 22 | 17 |
| 23 | 9 |
| 24 | 20 |
| 25 | 8 |
| 26 | 18 |
| 27 | 41 |
| 28 | 9 |
| 29 | 7 |
| 30 | 12 |
| 31 | 17 |
| 32 | 14 |
| 33 | 13 |
| 34 | 9 |
| 35 | 15 |
| 36 | 17 |
| 37 | 22 |
| 38 | 18 |
| 39 | 28 |
| 40 | 4 |
| 41 | 19 |
| 42 | no example |
| 43 | 13 |
| 44 | 7 |
| 45 | 12 |
| 46 | 10 |
| 47 | 21 |
| 48 | no example |
| 49 | 10 |
| 50 | 16 |
| 51 | 10 |
| 52 | 5 |
| 53 | 6 |
| 54 | 11 |
| 55 | 13 |
| 56 | 13 |
| 57 | 18 |
| 58 | 19 |
| 59 | 4 |
| 60 | 11 |
| 61 | 11 |
| 62 | 12 |

-continued

| Test Polymer | Percentage of Paper Stained |
|---|---|
| 63 | 6 |
| 64 | 6 |
| 65 | 18 |
| 66 |  |
| 67 | 18 |
| 68 | 15 |
| 69 | 13 |
| 70 | 14 |
| 71 | 10 |
| 72 | 15 |
| 73 | 7 |
| 74 | 6 |
| 75 | 7 |
| 76 | 13 |
| 77 | 15 |
| 78 | 22 |
| 79 | 8 |
| 80 | 21 |
| 81 | 9 |
| 82 | 8 |
| 83 | 9 |
| 84 | 13 |
| 85 | 6 |
| 86 | 14 |
| 87 | 12 |
| 88 | 9 |
| 89 | 7 |
| 90 | 5 |
| 91 | 18 |
| 92 | 13 |
| 93 | 11 |
| 94 | no example |
| 95 | 9 |
| 96 | 12 |
| 97 | 13 |
| 98 | 2 |

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims

What is claimed is:

1. A method of treating obesity in a mammal comprising the step of orally administering to the mammal an effective amount of at least one lipase inhibitor and a fat binding polymer, salt, or copolymer thereof, characterized by a repeat unit having the formula:

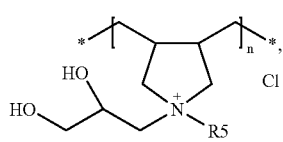

(VII)

wherein R5=H, or an alkyl chain from $C_1$ to $C_{22}$.

2. The method of claim 1 wherein R5=$CH_3$.

3. The method of claim 1 wherein said polymer is Poly(N,N-diallyl-N-methyl-N-(2,3-dihydroxypropyl) ammonium chloride).

4. The method of claim 3 wherein said lipase inhibitor is tetrahydrolipstatin.

5. A method for treating steatorrhea in a mammal comprising the step of orally administering to the mammal a therapeutic amount of a polymer characterized by having a repeat unit having the formula:

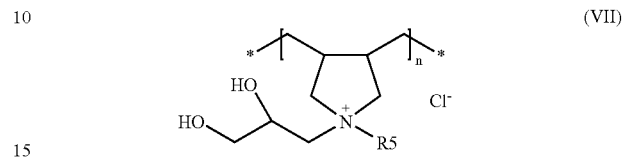

(VII)

wherein R5=H, or an alkyl chain from $C_1$ to $C_{22}$.

6. A method for treating hypertriglyceridemia in a mammal comprising the step of administering to the mammal a therapeutically effective amount of at least one lipase inhibitor and a polymer characterized by a combination of repeat units having the formula

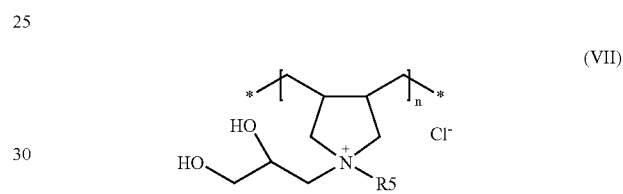

(VII)

Wherein R5=H, or an alkyl chain from $C_1$ to $C_{22}$, in combination with at least one lipase inhibitor.

7. A method for reducing the absorption of dietary fat in a mammal comprising the step of orally administering to the mammal a therapeutically effective amount of at least one lipase inhibitor in combination with a polymer characterized by a combination of repeat units having the formula

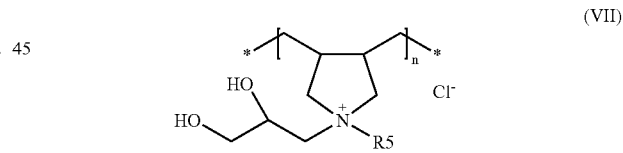

(VII)

Wherein R5=H, or an alkyl chain from $C_1$ to $C_{22}$.

8. A method of treating obesity in a mammal comprising the step of orally administering to a mammal an effective amount of a polymer, salt, or copolymer thereof, characterized by a repeat unit having the formula:

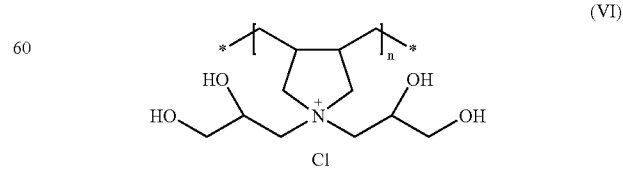

(VI)

in combination with at least one lipase inhibitor.

9. The method of claim 8 wherein said lipase inhibitor is tetrahydrolipstatin.

10. A method for treating steatorrhea in a mammal comprising the step of orally administering to the mammal a therapeutic amount of a polymer characterized by having a repeat unit having the formula:

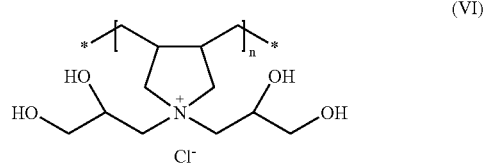

(VI)

11. A method for treating hypertriglyceridemia in a mammal comprising the step of administering to the mammal a therapeutically effective amount of at least one lipase inhibitor and a polymer characterized by a combination of repeat units having the formula:

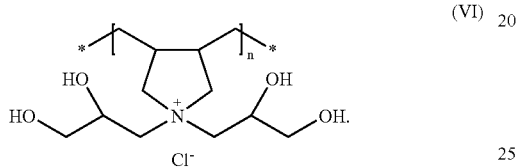

(VI)

12. A method for reducing the absorption of dietary fat in a mammal comprising the step of orally administering to the mammal a therapeutically effective amount of at least one lipase inhibitor and a polymer characterized by a combination of repeat units having the formula:

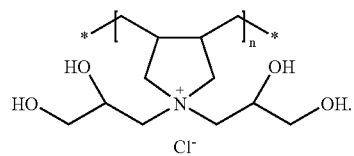

13. The method of claim 8 wherein said polymer is as Poly(N,N-diallyl-N,N-di(2,3-dihydroxypropyl)ammonium chloride).

* * * * *